United States Patent
Dubey et al.

(10) Patent No.: US 7,078,532 B2
(45) Date of Patent: Jul. 18, 2006

(54) PROCESS FOR MANUFACTURE OF FOSINOPRIL SODIUM

(75) Inventors: Sushil Kumar Dubey, Madhya Pradesh (IN); Saswata Lahiri, Madhya Pradesh (IN); Anil Vir Singh, Madhya Pradesh (IN)

(73) Assignee: Lupin Laboratories Limited, Pradesh (IN)

( * ) Notice: Subject to any disclaimer, the term of this patent is extended or adjusted under 35 U.S.C. 154(b) by 417 days.

(21) Appl. No.: 10/297,224

(22) PCT Filed: Aug. 17, 2001

(86) PCT No.: PCT/IN01/00144

§ 371 (c)(1),
(2), (4) Date: Jun. 17, 2003

(87) PCT Pub. No.: WO02/088149

PCT Pub. Date: Nov. 7, 2002

(65) Prior Publication Data

US 2004/0225127 A1    Nov. 11, 2004

(30) Foreign Application Priority Data

Apr. 30, 2001    (IN) .................................. 411/2001

(51) Int. Cl.
*C07F 9/553* (2006.01)

(52) U.S. Cl. ...................................................... 548/413

(58) Field of Classification Search ................. 548/413
See application file for complete search history.

(56) References Cited

U.S. PATENT DOCUMENTS

| 4,337,201 | A | * | 6/1982 | Petrillo, Jr. ................. 548/413 |
| 4,873,356 | A | * | 10/1989 | Petrillo et al. .............. 558/180 |
| 5,008,399 | A | * | 4/1991 | Sedergran ................... 548/413 |

* cited by examiner

*Primary Examiner*—Golam M. M. Shameem
(74) *Attorney, Agent, or Firm*—Ladas & Parry LLP

(57) ABSTRACT

The present invention discloses a process for the synthesis of fosinopril as a single desired isomer of high purity in two steps comprising of (a) preparation of fosinopril as a mixture of four diastereomers and (b) separation of the desired isomer from the mixture through formation of alkali metal salts followed by crystallisation.

30 Claims, 4 Drawing Sheets

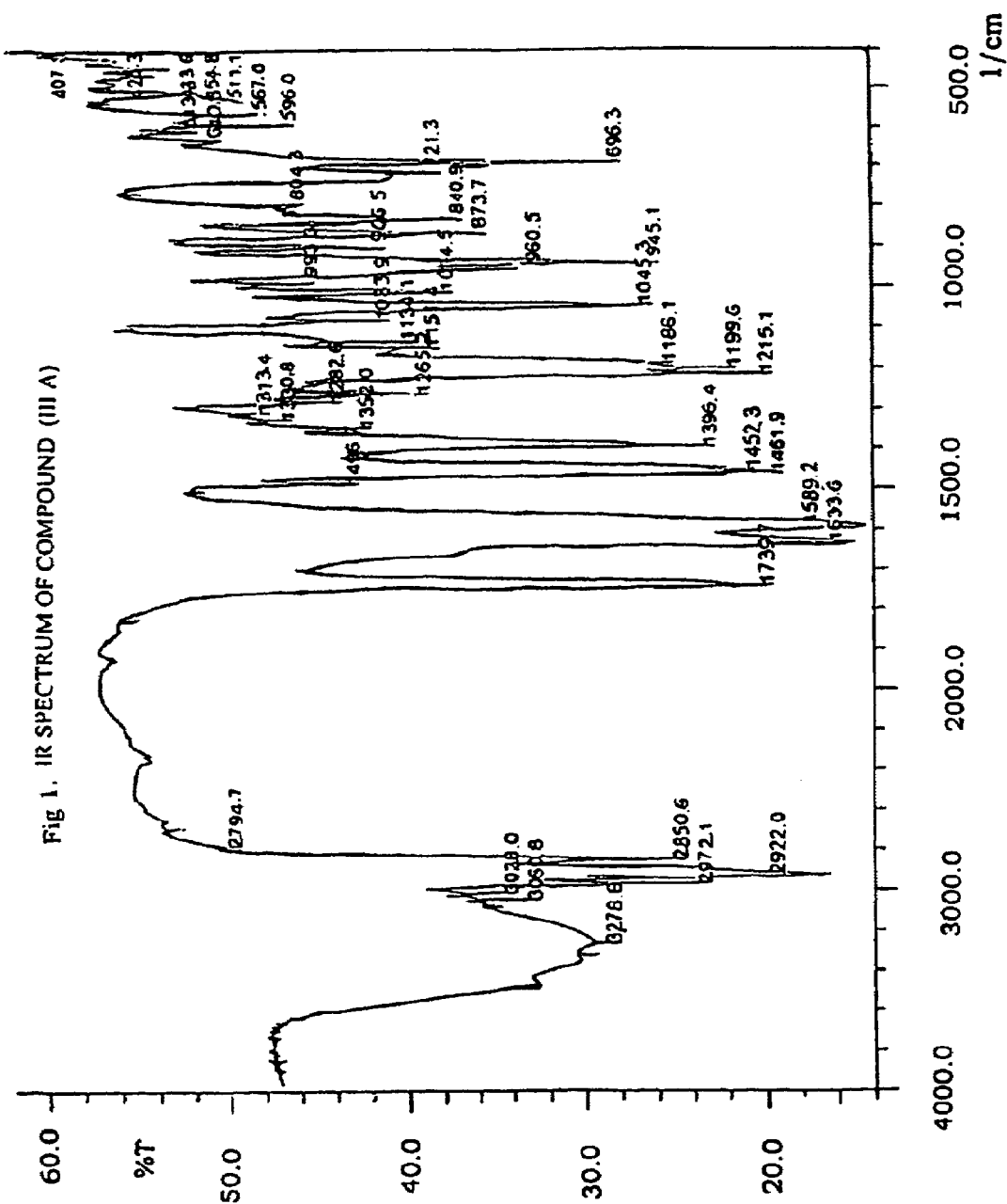
Fig 1. IR SPECTRUM OF COMPOUND (III A)

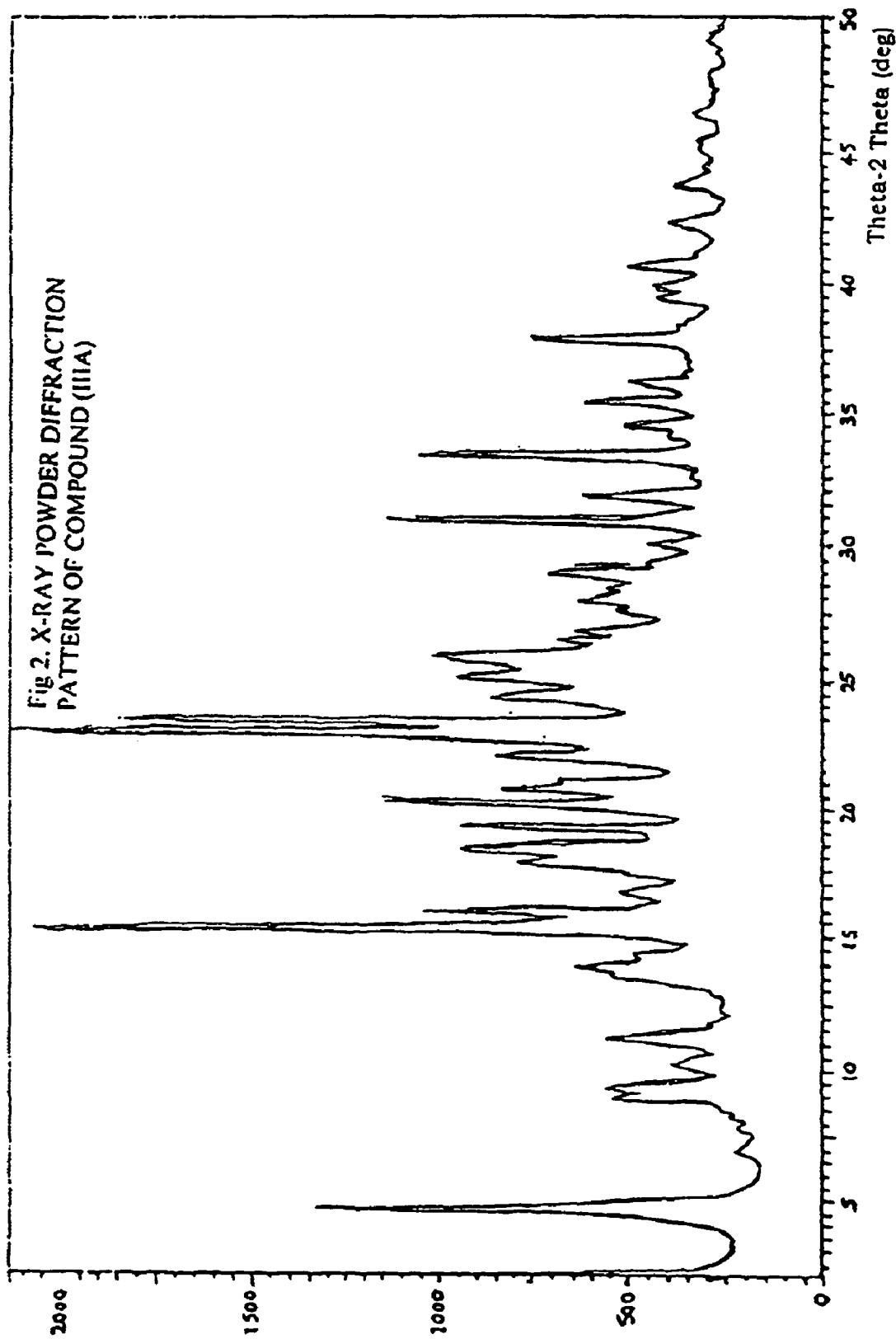

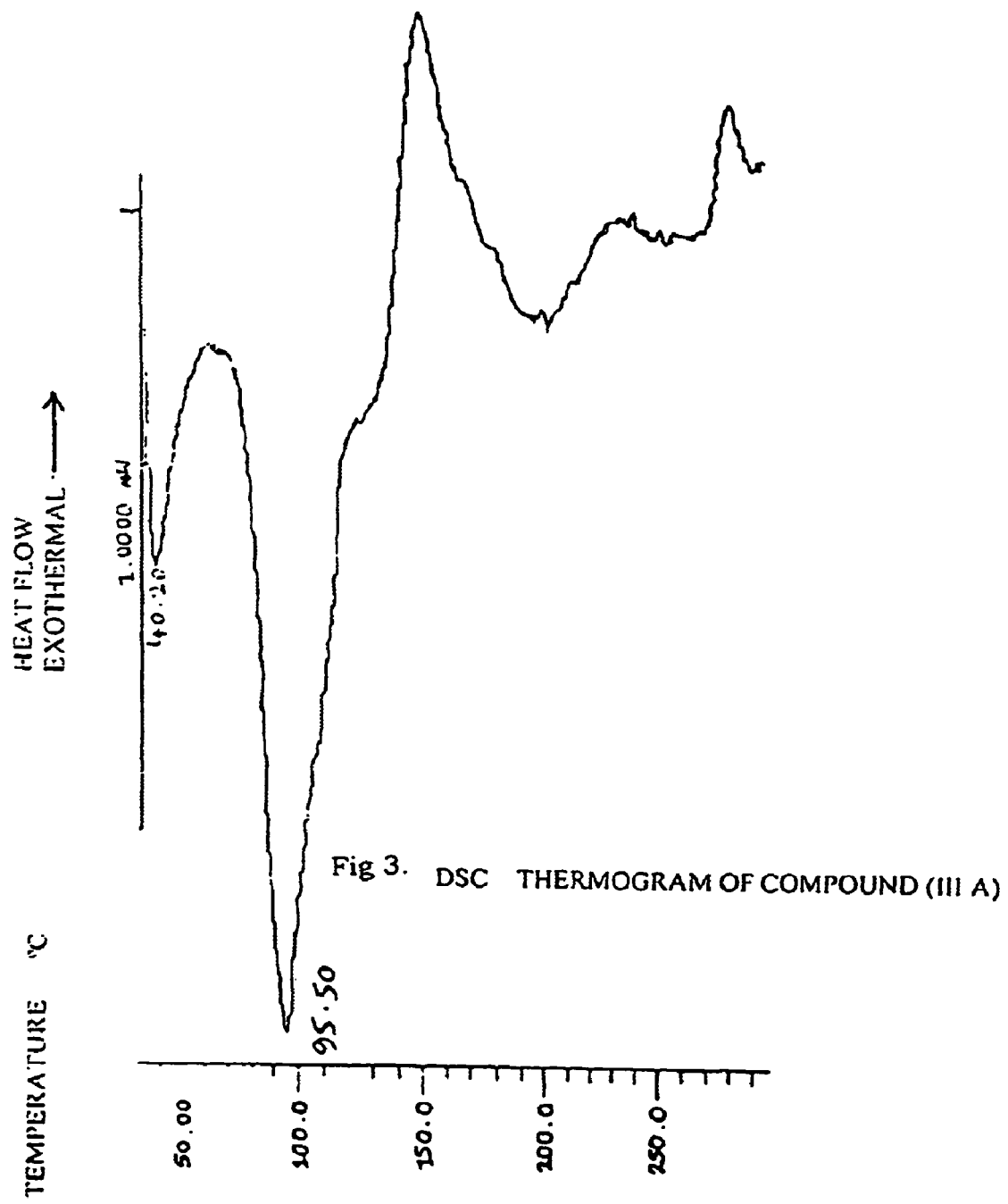
Fig 3. DSC THERMOGRAM OF COMPOUND (III A)

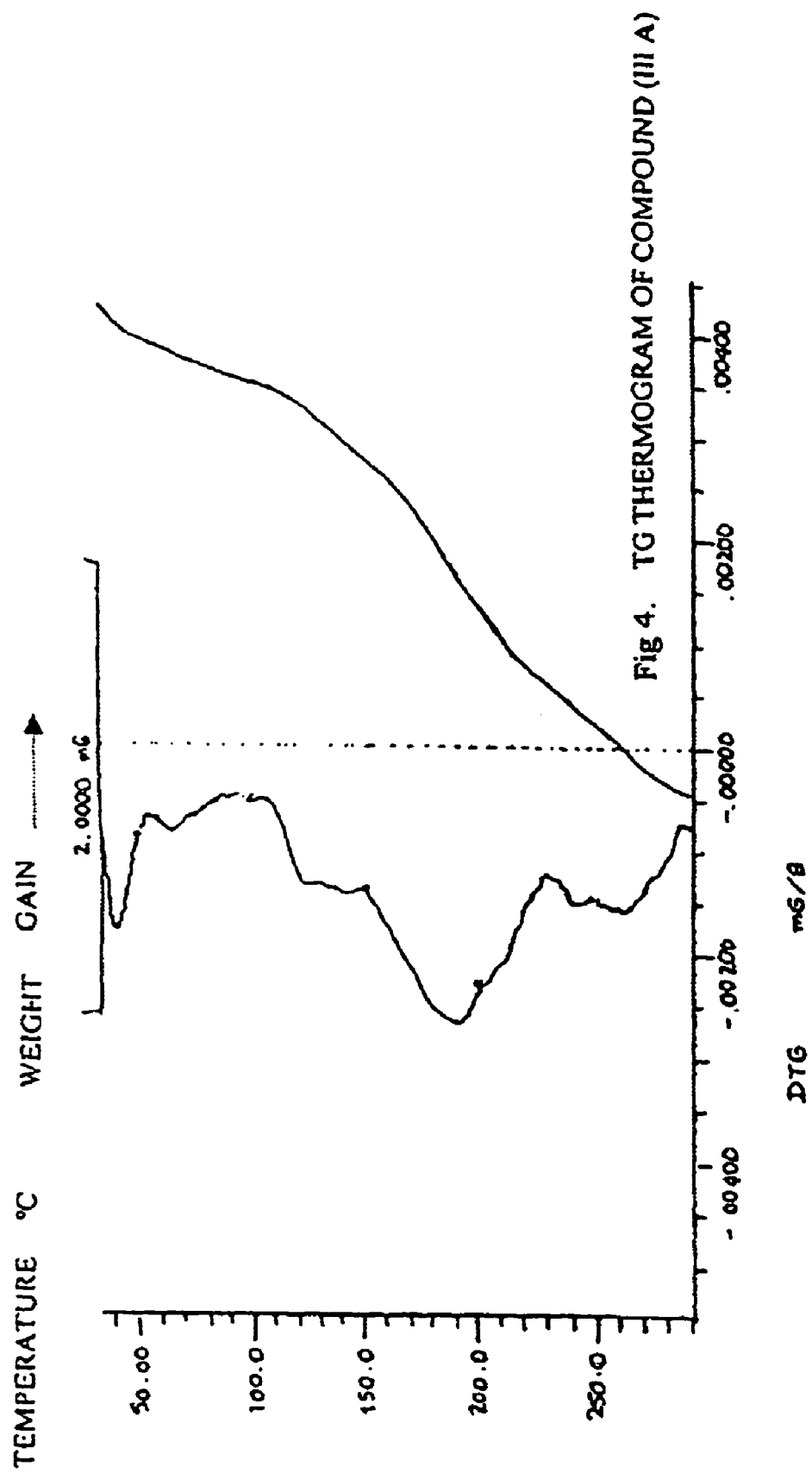
Fig 4. TG THERMOGRAM OF COMPOUND (III A)

PROCESS FOR MANUFACTURE OF FOSINOPRIL SODIUM

This is a 371 OF PCT/IN01/00144 filed Aug. 17, 2001 which designated the U.S., claims the benefit thereof and incorporates the same by reference.

The invention relates to an improved process for the synthesis of the angiotensin converting enzyme (ACE) inhibitor, fosinopril sodium of formula (I) in high purity.

BACKGROUND OF THE INVENTION

U.S. Pat. No. 4,337,201 (Petrillo, Jr. et. al.) describes certain esters of phosphinylalkanoyl prolines or phosphinylalkanoyl substituted prolines as inhibitors of angiotensin converting enzyme (ACE). These enzymes convert angiotensin I into angiotensin II, the latter being a powerful vasoconstrictor causing hypertension. Inhibition of ACE results in reduction of blood pressure, thereby improving the quality of life of the patient susceptible to or suffering from hypertension.

Among the phosphinylalkanoyl esters described in U.S. Pat. No. 4,337,201 is the compound generically known as fosinopril sodium, marketed under the brand name Monopril®. Fosinopril sodium is administrated orally either alone or in combination with diuretics for treatment of hypertension. It is also used as an adjunct in the treatment of congestive heart failure.

Fosinopril is an optically active compound having total four centres of asymmetry, three on carbon and one on phosphorous atom. Out of the sixteen isomers possible for this compound, only one of the isomers is a therapeutic i.e. a pharmaceutical. The desired isomer possessing therapeutic value is [1[S*(R*)], 2α,4β]-4-cyclohexyl-1-[[[2-methyl-1-(1-oxopropoxy)propoxy](4-phenylbutyl)phosphinyl]acetyl]-L-proline, mono-sodium salt and accordingly fosinopril sodium is represented by formula (I).

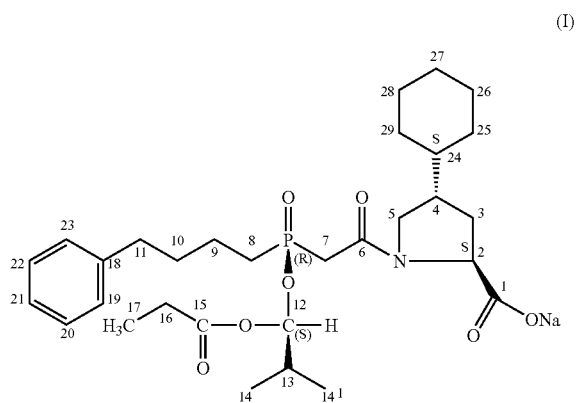

(I)

The prior art methods for synthesis of fosinopril, essentially consists of the following:

(i) Petrillo, Jr. et. al. in U.S. Pat. No. 4,337,201 discloses a process for preparation of phosphinyl alkanoyl proline esters of general formula (3) comprising of reacting a phosphinyl acetic acid of formula (1) with a proline derivative of formula (2), the coupling reaction being accomplished using known amide forming procedures.

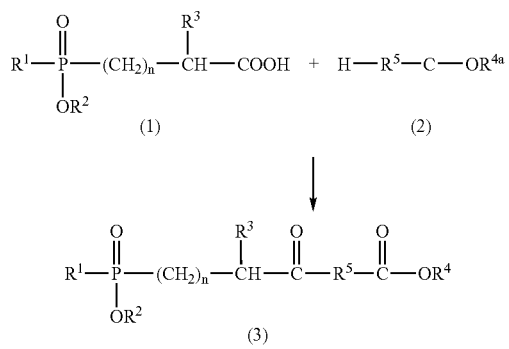

Alternatively, compound of formula (3) is prepared by alkylation of the hydroxy compound of formula (4) with a halo compound of formula (5), followed by basic hydrolysis.

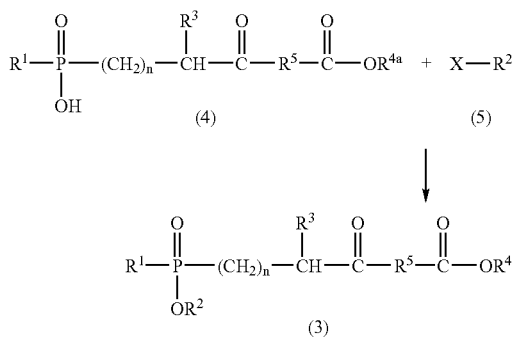

In compounds of formula (1) to (5) mentioned hereinbefore synthesis of fosinopril is achieved and completed when $R^1$ is phenylbutyl; $R^2$ is isobutylpropionate; $R^3$ is hydrogen; $R^{4a}$ is alkyl or arylalkyl, preferably benzyl; $R^4$ is hydrogen; $R^5$ is 4-cyclohexyl proline, n is zero and X is halogen.

However, this patent does not:

(a) even remotely suggest any method for synthesising to specifically obtain the desired isomer of fosinopril sodium (I), thus making it clear that the product obtained by the methods described in the patent is a mixture of either all possible sixteen isomers or is a mixture of some of the possible isomers, (b) suggest, teach or disclose any method for separating the desired isomer of fosinopril from the mixture of isomers and (c) suggest, teach or disclose any synthesis of esters of phosphinyl alkanoyl prolines with the cycloalkyl group at the 4-position of the proline ring having a (trans) configuration. All examples described in the patent relate to synthesis of such esters with the said cycloalkyl group having a (cis) configuration. The (trans) configuration of the cyclohexyl ring is required in fosinopril sodium.

(ii) Petrillo, Jr. et. al. in U.S. Pat. No. 4,873,356 describe a method for synthesis of the desired isomer of fosinopril sodium (I), which is an improvement over the general method described in U.S. Pat. No. 4,337,201.

It addresses the shortcomings associated with the said U.S. Pat. No. 4,337,201.

The method disclosed in this patent comprises of alkylating a phosphinyl acetic acid derivative of formula (6) with a haloester of formula (7) in the presence of an organic base selected from triethylamine, pyridine, tripropylamine and DBU to give the corresponding ester of formula (8) as a mixture of two diastereomers. The carboxylic acid ester protective group is removed by hydrogenolysis to give the phosphinyl acetic acid compound of formula (9), which is obtained as mixture of a pair of racemic forms i.e. a mixture of two diastereomers, namely a mixture of compounds of formula (9 A) and its mirror image (9 B); (9 C) and its mirror image (9 D).

The racemic mixture of compounds (9 A) and its mirror image (9 B) is separated from the other pair (9 C) and its mirror image (9 D) by recrystallisation from suitable solvents such as isobutyl acetate or methyl isobutyl ketone, which is further resolved by treatment with optically active amines such as L-cinchonidine or other conventional resolving agents to give the resolved salt of enantiomer (9 B). Treatment with a strong acid gives the pure phosphinyl acetic acid isomer (9 B), the desired addendum for further elaboration to fosinopril sodium.

Thus, the pure single isomer (9 B) when reacted with trans)-4-cyclohexyl-L-proline gives fosinopril, which is converted to the sodium salt of formula (I) by conventional methods.

The chemistry practised in U.S. Pat. No. 4,873,356 is schematically summarised in Scheme-1.

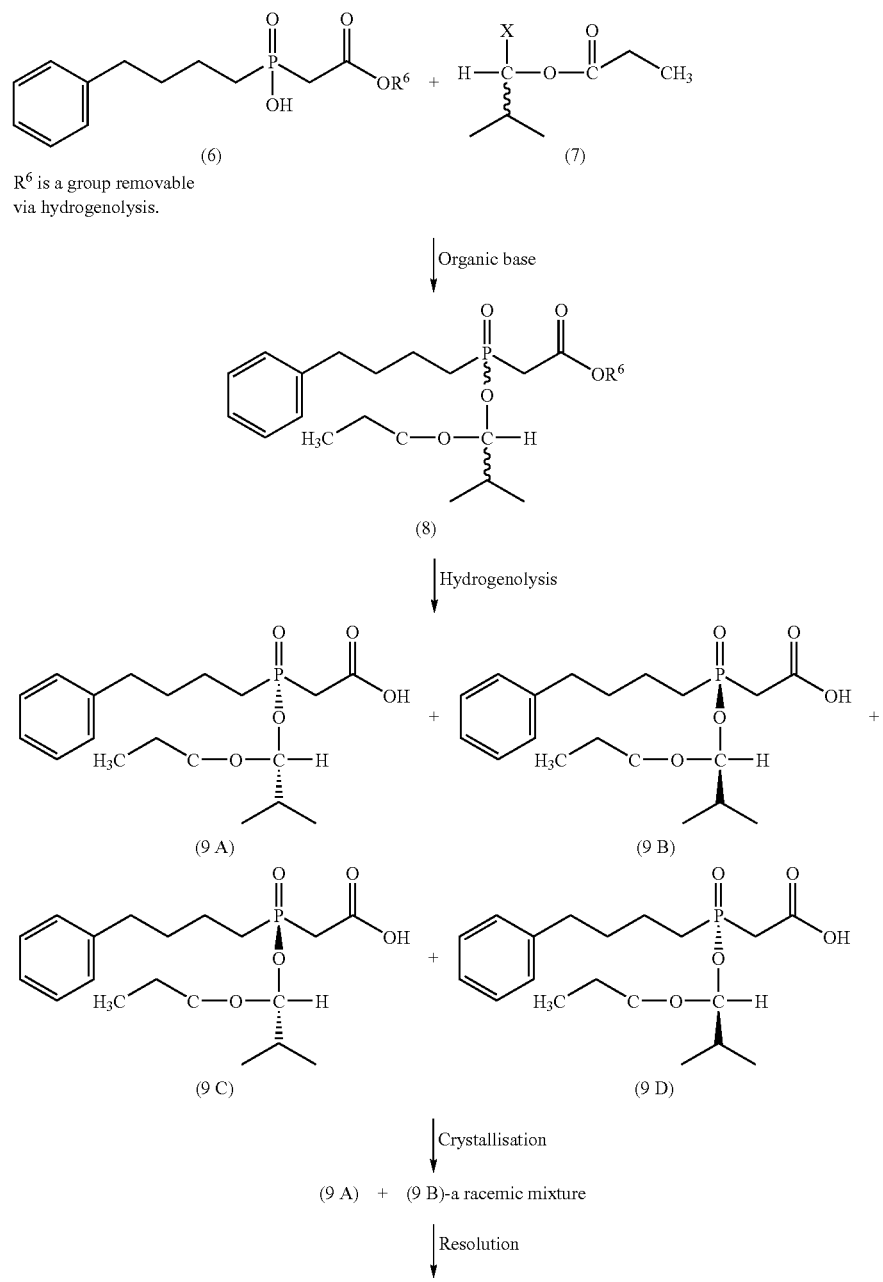

-continued (9 B)-Resolving Agent

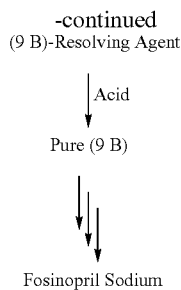

Fosinopril Sodium

U.S. Pat. No. 4,873,356 further claims that compound (8) including all stereomers thereof, compound (9), including all stereomers thereof i.e. compound (9 A) and its mirror image (9 B); compound (9 C) and its mirror image (9 D) and the intermediate salt of compound (9 B) with the resolving agent are all novel compounds.

This further substantiates the earlier observation that separation of such racemic mixtures or diastereomeric mixtures formed in the reaction was never meant to be a part of the spirit and scope of the process(es) disclosed in U.S. Pat. No. 4,337,201.

(i) U.S. Pat. No. 5,008,399 (Sedergran et. al.) describes a process which is an improvement over that disclosed in U.S. Pat. No. 4,873,356. The improvement effected comprises carrying out the reaction of compound (6) and compound (7) in the presence of organic bases such as 4-methylmorpholine, diazabicyclooctane, quinuclidine, 1-methylpyrolidine or cinchonidine to give compound (8) as a mixture of four isomers, which on hydrogenolysis gives compound (9) as a mixture of two diastereomeric pairs i.e. a mixture of compounds (9 A) and its mirror image (9 B); (9 C) and its mirror image (9 D). The diastereomeric pair is separated and resolved as described in U.S. Pat. No. 4,873,356 to give the pure isomer (9 B).

U.S. Pat. No. 5,008,399 claims that by utilising the organic bases mentioned therein an increase in diastereoselectivity is achieved affording the racemic mixture of compounds (9 A) and its mirror image (9 B) in a ratio of 1.5 over the other racemic mixture i.e. (9 C) and its mirror image (9 D). This is an improvement over a ratio of 1.2 achieved by employing a base such as triethylamine as disclosed in U.S. Pat. No. 4,873,356. An overall increase in efficiency of preparing fosinopril sodium (I) is thus achieved.

The processes described in U.S. Pat. Nos. 4,873,356 and 5,008,399, while leading to the synthesis of fosinopril sodium having the desired optical purity, are associated with the following disadvantages. In particular, the processes of this patent:

involves separation of isomers that are mirror images of each other i.e. enantiomers or a racemic mixture (9 A) and its mirror image (9 B) from (9 C) and its mirror image (9 D)

requires optical resolution for further separation of the enantiomers (9 A).

requires optical resolution for further separation of the enantiomers (9 A) and its mirror image (9 B), involves considerable wastage of the desired isomer (9 B) and utilisation of expensive resolving agents (one to two molar equivalents) and organic bases (about two molar equivalents), in the separation of enantiomers followed by optical resolution thereby resulting in an overall decrease in efficiency and increase in the cost of manufacture of the end product i.e. fosinopril sodium and do not teach or disclose any method for recycling of the unwanted isomers (9 A), (9 C) and (9 D) back to the desired isomer (9 B).

(i) Besides the aforementioned process patents, various methods are reported for preparation of key intermediates required for synthesis of fosinopril. For instance, U.S. Pat. No. 4,168,267 (Petrillo, Jr., et. al.), U.S. Pat. No. 4,384,123 (Petrillo. Jr., et. al.), U.S. Pat. No. 4,448,772 (Karanewsky et. al.), U.S. Pat. No. 4,594,199 (Thottathil et. al.) and U.S. Pat. No. 4,602,092 (Thottathil et. al.) disclose processes for synthesis of the phosphinyl acetic acid fragment of fosinopril. U.S. Pat. No. 4,316,905 (Krapcho et. al.), U.S. Pat. No. 4,501,901 (Thottathil et. al.), U.S. Pat. No. 4,588,819 (Thottathil et. al.), U.S. Pat. No. 4,734,508 (Thottathil et. al.), U.S. Pat. No. 4,912,230 (Anderson et. al.), U.S. Pat. No. 4,912,231 (Kronenthal et. al.) and U.S. Pat. No. 4,937,355 (Kloss et. al.) describe processes for synthesis of the optically active (cis/trans)-4-cyclohexyl-L-proline fragment.

(ii) In addition, it is known that the sodium salt of fosinopril can exist in two polymorphic forms, designated as Form-A and Form-B. The polymorphic forms differ in their respective solid state IR, $^{13}C$ NMR and $^{31}P$ NMR spectra as well as X-ray (powder) diffraction patterns. Of the two forms, Form-A, which is the therapeutic is believed to be thermodynamically more stable. No other polymorphic form for fosninopril sodium has been reported so far.

(iii) U.S. Pat. No. 5,162,543 (Grosso et. al.) discloses a selective process for preparation of any one of the two polymorphs of fosinopril sodium as well as a process for inter conversion of one form into the other. Polymorphic Form-A is obtained by crystallisation of fosinopril sodium in a keto or hydroxylic solvent or a mixture thereof in presence of water, the requirement being water should constitute $\geq 2\%$ or more of the total solvent(s). When the crystallisation is carried out in a keto or hydroxylic solvent or a mixture thereof, wherein the water content is $\leq 0.2\%$ Form-B is obtained. Rapid evaporation of a methanolic solution of Form-A containing $\leq 0.2\%$ of water converts it to the other form i.e. Form-B.

(iv) The inference one draws from the methods described in U.S. Pat. No. 5,162,543 is that the formation of the respective polymorphs is not only dependent on the solvent employed but also on the amount of water present in the solvents(s).

H. G. Brittain et. al. [*Journal of Pharmaceutical & Biomedical Analysis*, 1993, Vol 11 (No. 11/12), pp 1063–1069] describe methods for preparation of the two polymorphic forms. For instance, Form-A is obtained by crystallisation of fosinopril sodium from various organic solvents such as acetone, acetonitrile, alcohols and the like containing water. The authors claim that formation of this polymorphic form is independent of the solvent used as long as the crystallisation is slow. There is no mention on the amount of water that is necessary for formation of this form.

Form-B, on the other hand, is obtained by rapid/flash evaporation of the solvent from a solution of fosinopril sodium in that solvent.

There are no reports available on the existence of polymorphic forms for other salts of fosinopril, such as alkali metal salts with lithium, potassium, rubidium and cesium or alkaline earth metal salts with beryllium, magnesium, calcium, strontium and barium or salts of fosinopril with heavy metals.

Thus, to summarise the prior art:
a) the general methods described in U.S. Pat. No. 4,337,201 lead to a mixture of all possible sixteen isomers or mixture of some of the possible isomers of fosinopril. No method for separation and isolation of the pure desired isomer is mentioned,
b) the specific methods disclosed in U.S. Pat. Nos. 4,873,356 and 5,008,399, lead to formation of only four isomers of fosinopril. However, enantiomers, which are mirror images of each other are separated from the mixture,
c) separation of the pure desired isomer from the racemic mixture calls for optical resolution,
d) optical resolution leads to considerable wastage of the desired isomer leading to low efficiency and increase in cost of manufacture,
e) no method is described for recycling of the unwanted isomers back to the desired one, and
f) formation of polymorphic Form-A of fosinopril sodium is dependent on the solvent(s) employed and the amount of water present in the solvent(s).

A need, therefore, exists for a method for the synthesis of fosinopril sodium, which in addition to eliminating/minimising the disadvantages, specially optical resolution associated with the prior art methods, provides a cost-effective and convenient method for synthesis of the objective compound.

SUMMARY OF THE INVENTION

Accordingly, in one aspect, the present invention provides a method for synthesis of fosinopril as the desired single isomer comprising a) reacting a phosphinyl acetic acid derivative of formula (IV)

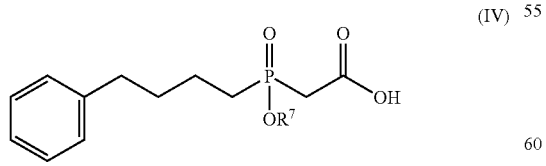

wherein $R^7$ is lower alkyl of 1–4 carbon atoms with (trans)-4-cyclohexyl-L-proline of structure (V) or a salt thereof, the carboxylic acid group of which is activated by formation of its mixed anhydride, in presence of a base and an organic solvent

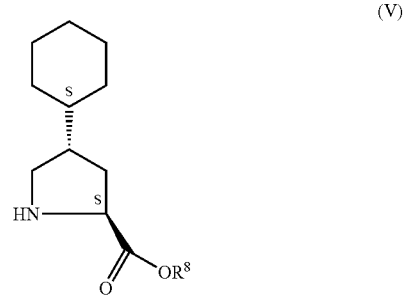

wherein $R^8$ is a group easily removable by hydrogenolysis and is benzyl or benzyl substituted at ortho, meta or para positions by an alkyl) alkoxy, alkanoyl, phenyl, nitro or dialkylamino group to give the phosphinyl acetamido proline derivative of formula (VI), wherein $R^7$ is lower alkyl of 1–4 carbon atoms and removing the protective group $R^7$ to obtain phosphinyl acetamido proline derivative of formula (VI), wherein $R^7$ is hydrogen;

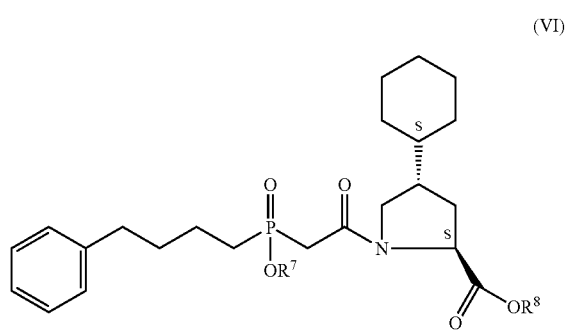

b) reacting a compound of formula (VI), wherein $R^7$ is hydrogen with a haloester of structure (VII),

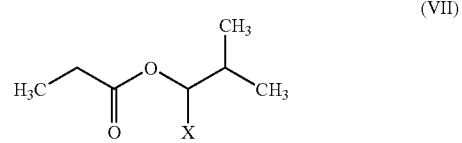

wherein X is halogen in the presence of an organic base and a solvent to give the phosphinylalkanoyl proline ester of formula (II$^a$)

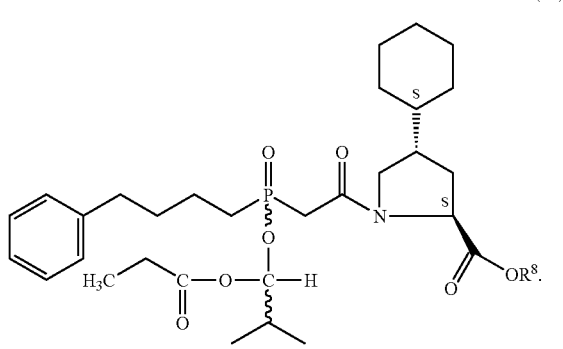

c) removing the protective group $R^8$ from the compound (II$^a$) thus obtained to give phosphinylalkanoyl proline ester i.e. fosinopril of formula (II) as a mixture of four diastereomers of formula (II A), (II B), (II C) and (II D).

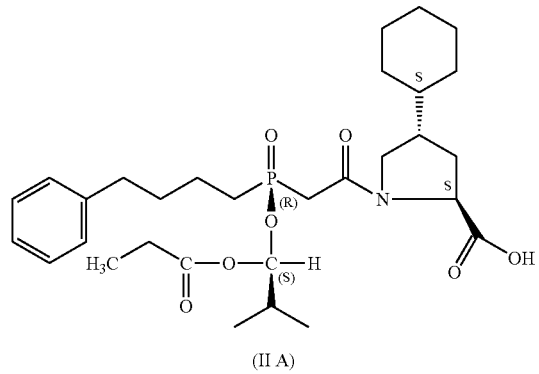

(II A)

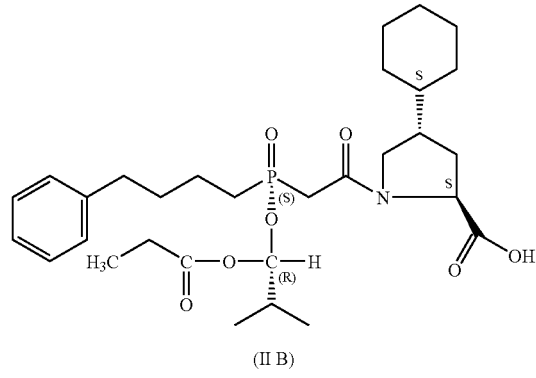

(II B)

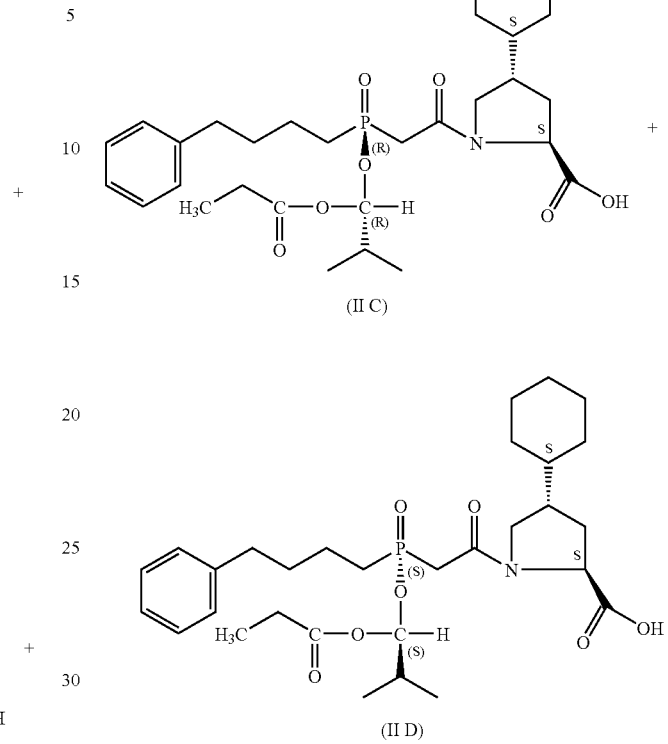

(II C)

(II D)

The chemistry utilised for synthesis of compound of formula (II) as a mixture of four diastereomers (II A), (II B), (II C) and (II D) is summarised in Scheme-II.

Scheme-II: Synthesis of fosinopril as a mixture of four diastereomers

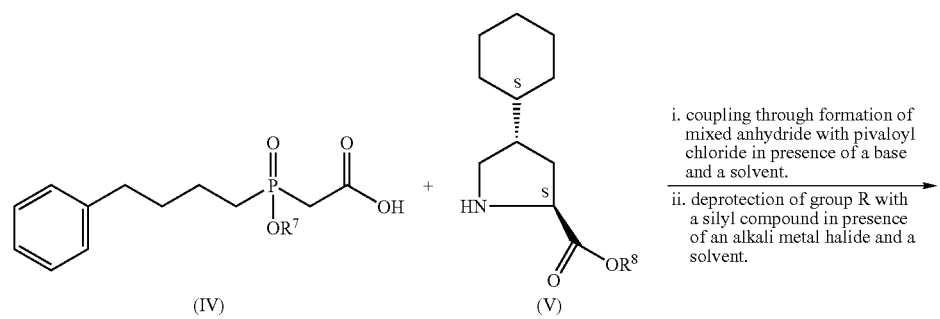

(IV)     (V)

i. coupling through formation of mixed anhydride with pivaloyl chloride in presence of a base and a solvent.
ii. deprotection of group R with a silyl compound in presence of an alkali metal halide and a solvent.

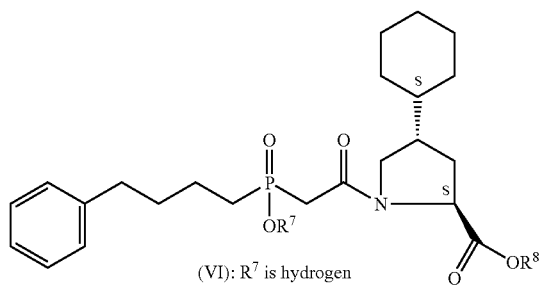

(VI): $R^7$ is hydrogen

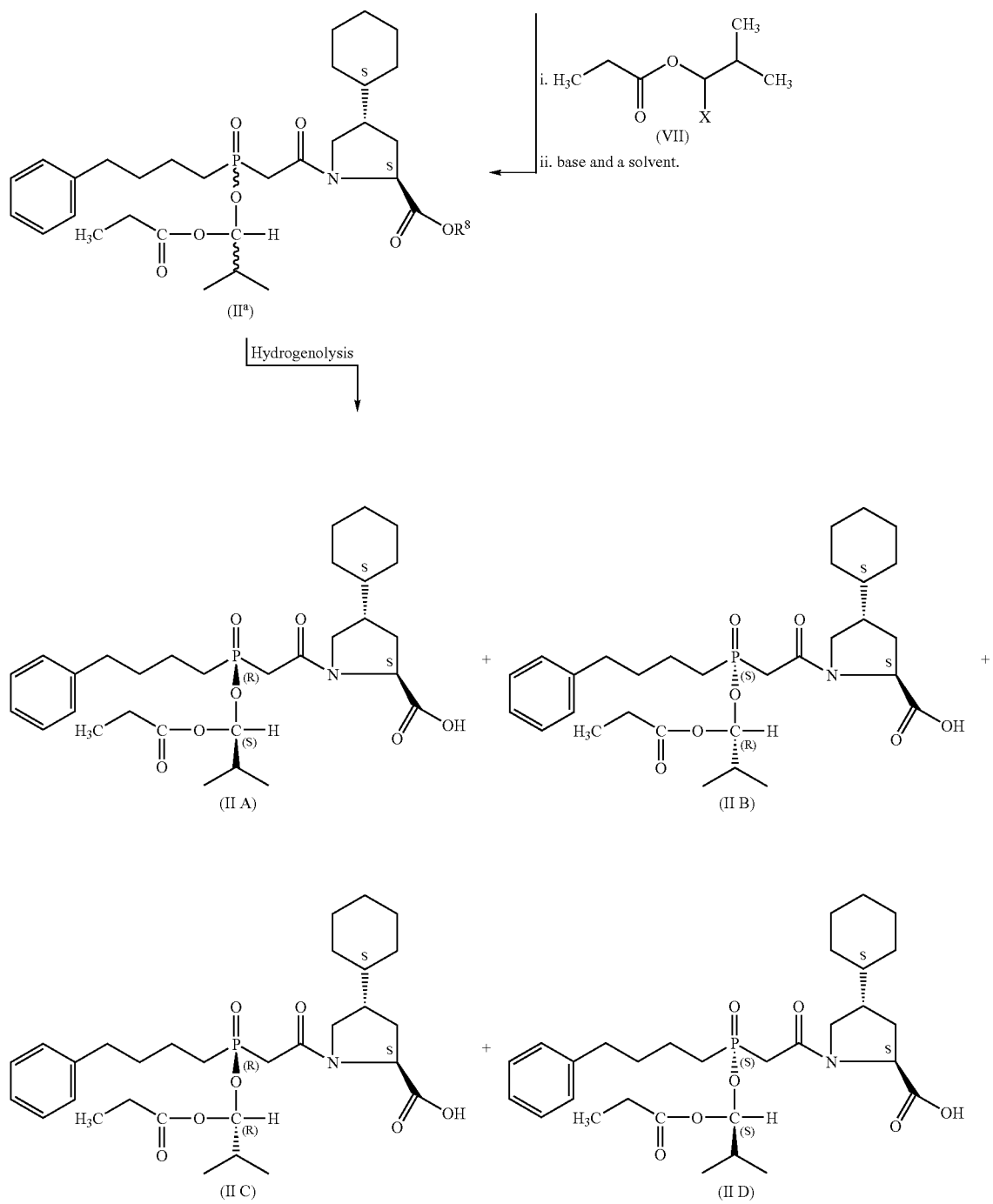

In another aspect of the present invention there is provided a one-step, cost-effective method as summarised in Scheme-III for separation of diastereomer (II A) in high purity from the mixture of four diastereomers (II A), (II B), (II C) and (II D) comprising d) mixing together the mixture of four diastereomers of formula (II A), (II B), (II C) and (II D) with a cesium salt in the presence of a solvent and crystallisation of the corresponding mixture of cesium salts of compounds (II A), (II B), (II C) and (II D) from the same solvent or a mixture of solvents in the presence of 1 to 10 moles of water to give the cesium salt of diastereomer (II A), isolated as the dihydrate of formula (III A) in high purity.

Scheme-III: Separation of the desired isomer (II A) from a mixture of four diastereomers (II A), (II B), (II C) and (II D)

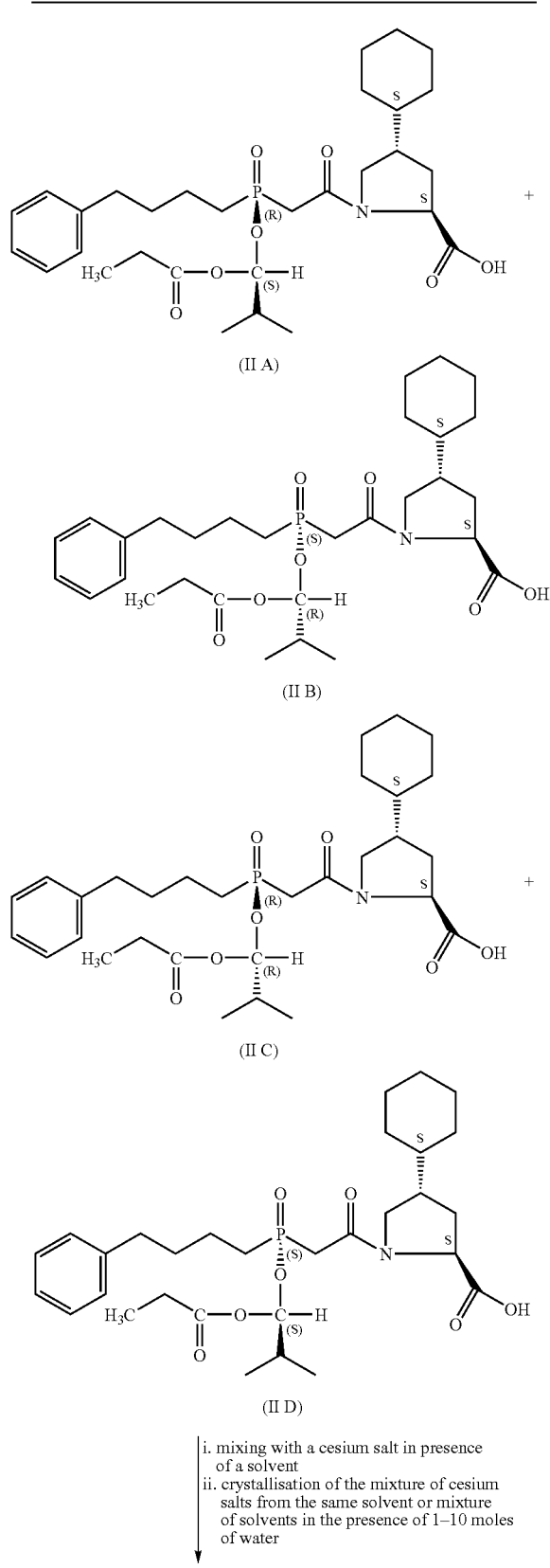

(II A)

(II B)

(II C)

(II D)

i. mixing with a cesium salt in presence of a solvent
ii. crystallisation of the mixture of cesium salts from the same solvent or mixture of solvents in the presence of 1–10 moles of water -continued

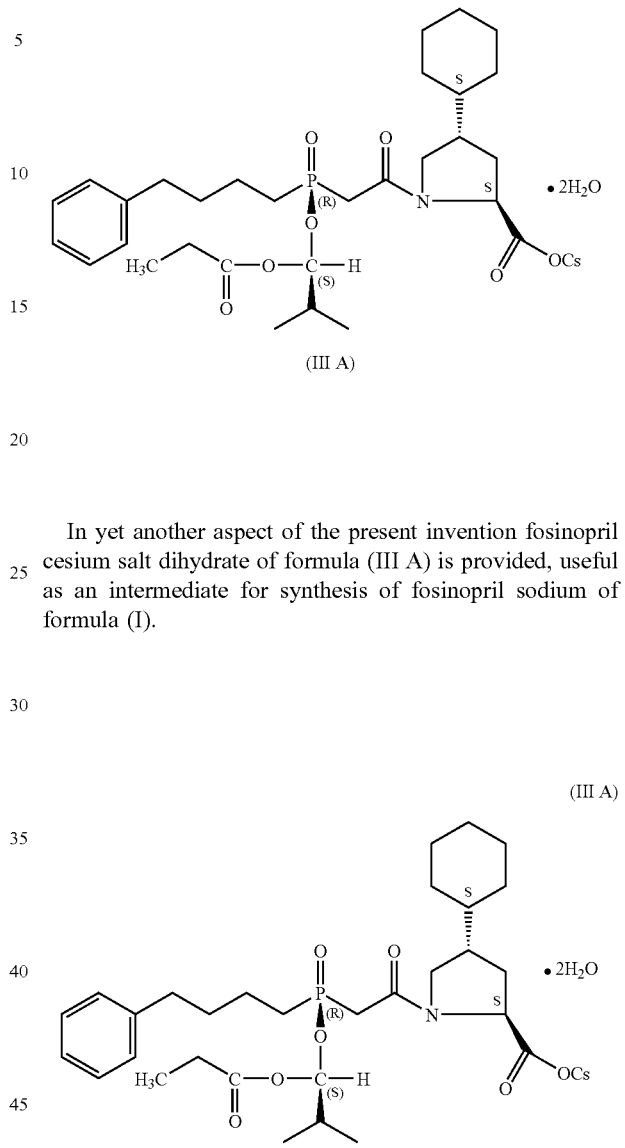

(III A)

In yet another aspect of the present invention fosinopril cesium salt dihydrate of formula (III A) is provided, useful as an intermediate for synthesis of fosinopril sodium of formula (I).

(III A)

Yet another aspect of the present invention is to provide a convenient method for preparation of fosinopril sodium of formula (I), predominantly in the polymorphic Form-A as summarised in Scheme-IV comprising e) reacting fosinopril cesium salt dihydrate of formula (III A) with an acid to give the corresponding free acid compound, f) mixing together the free carboxylic acid compound thus obtained with a sodium salt in the presence of organic solvent to give fosinopril sodium of formula (I) and g) slow crystallisation of fosinopril sodium thus obtained from a solvent containing water <0.2% over 10 to 24 hours to give fosinopril sodium polymorph A.

Scheme-IV: preparation of fosinopril sodium predominantly in the polymorphic Form-A from fosinopril cesium salt dihydrate.

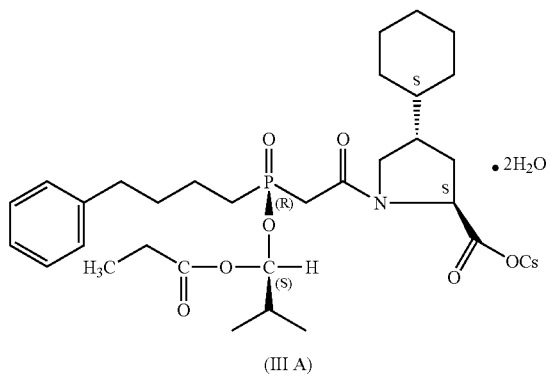

(III A)

i. conversion to the free carboxylic acid by treatment with an acid
ii. mixing the free acid compound with a sodium metal carrier in presence of a solvent to form the sodium salt
iii. slow crystallisation of fosinopril sodium from a solvent or mixture of solvents containing <0.2% water.

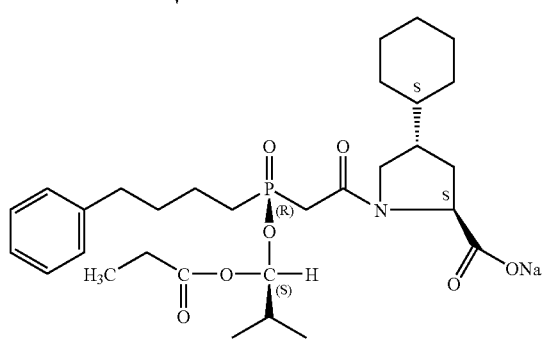

(I): Fosinopril sodium Polymorph A

In a further aspect of the present invention, a method is provided for recycling of the undesired fosinopril diastereomers of structure (II B), (II C) and (II D) from the waste stream back to fosinopril sodium of formula (I), predominantly in the polymorphic Form-A comprising h) subjecting the mixture of diastereomers of formula (II B), (II C) (II D) and (II A) or their alkali metal salts thereof contained in the waste stream mother liquor to hydrolysis to give a compound of formula (VIII)

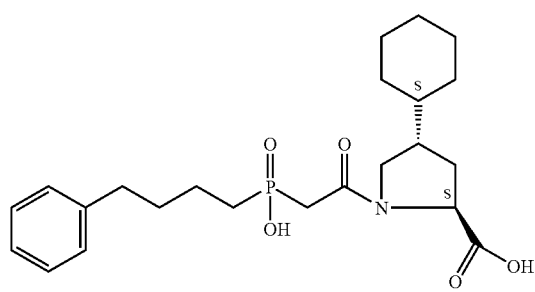

(VIII)

i) selective esterification of the carboxylic acid of compound (VIII) to give compound of formula (VI), wherein $R^8$ is a group easily removable by hydrogenolysis.

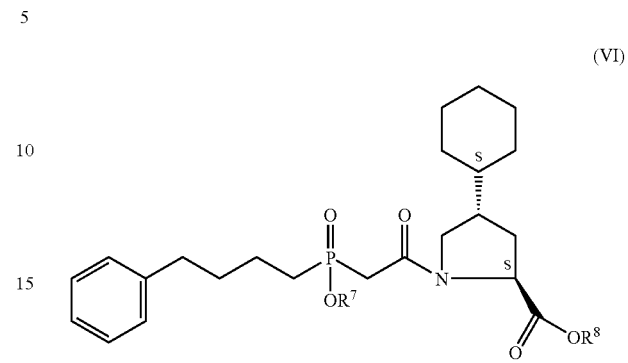

(VI)

j) alkylation of compound (VI) by reaction with a haloester of formula (VII), wherein X is halogen

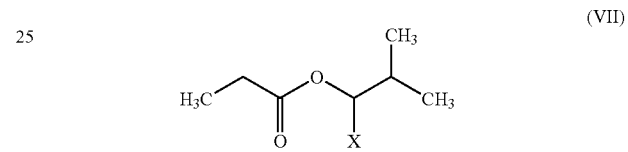

(VII)

in the presence of an an acid or base and a solvent give compound (II$^a$) which on hydrogenolysis gives phosphinylalkanoyl proline ester i.e. fosinopril (II) as a mixture of four diastereomers of formula (II A), (II B), (II C) and (II D) as described in sub-sections (b) and (c).

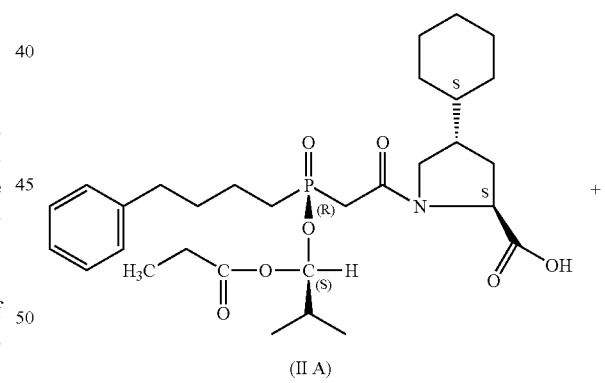

(II A)

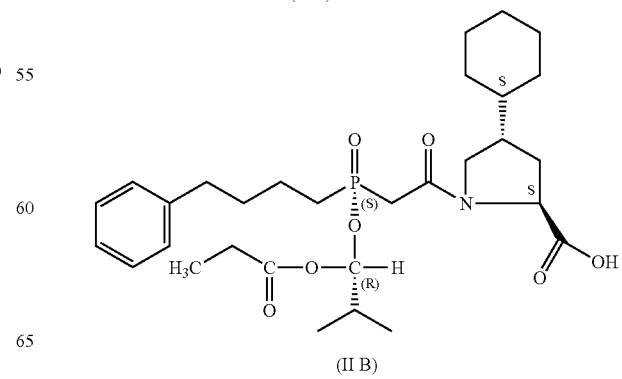

(II B)

-continued

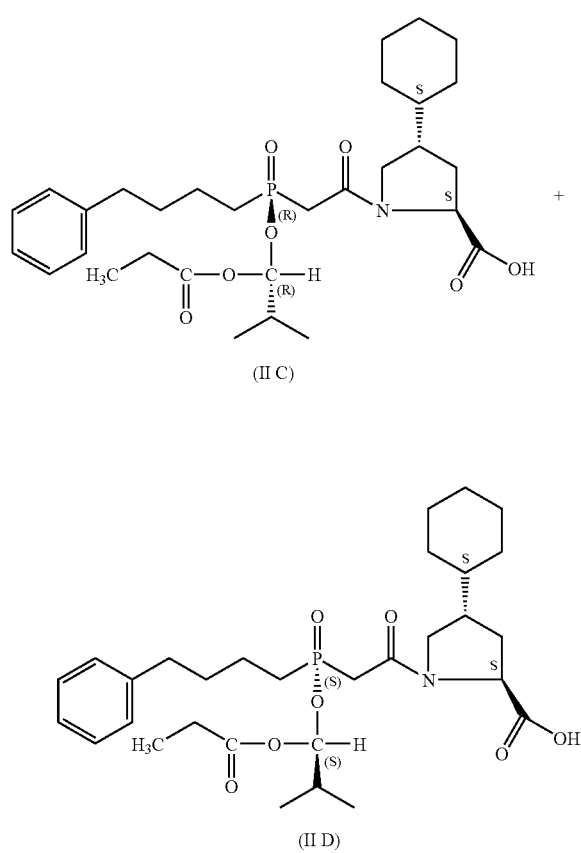

(II C)

(II D)

j) conversion of compound mixture of four diastereomers of formula (II A), (II B), (II C) and (II D) to the fosinopril cesium salt dihydrate of formula (III A) as described herein earlier in sub-section (d) and finally k) conversion of compound (III A) to fosinopril sodium polymorphic Form-A as described herein earlier in sub-sections (e) to (g).

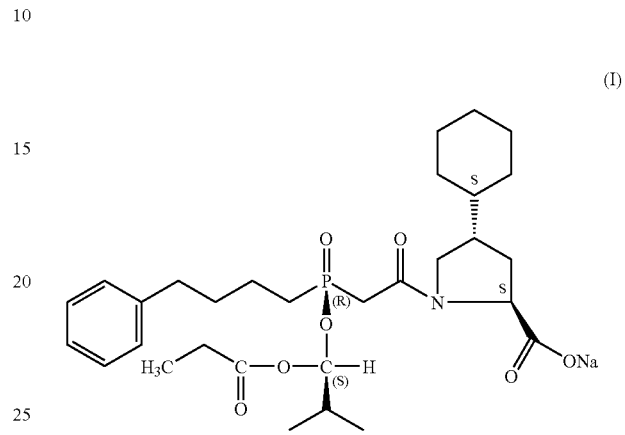

(I)

The method for recycling of waste isomers back to the desired therapeutic isomer is summarised in Scheme-V.

To the best of our knowledge, synthesis of fosinopril sodium in high optical and chemical purity employing the process described hereinbefore, specially comprising of separation of diastereomers rather than separation of enantiomers has not been reported so far.

Scheme-V: Recycling of unwanted isomers back to the desired isomer

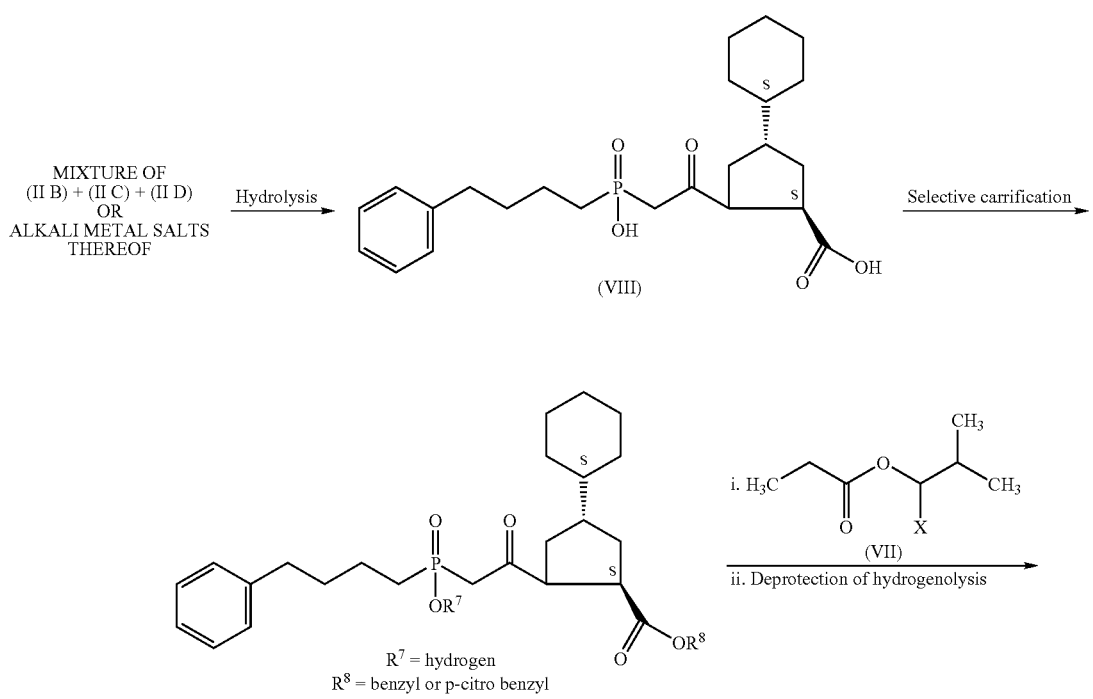

$R^7$ = hydrogen
$R^8$ = benzyl or p-citro benzyl

-continued

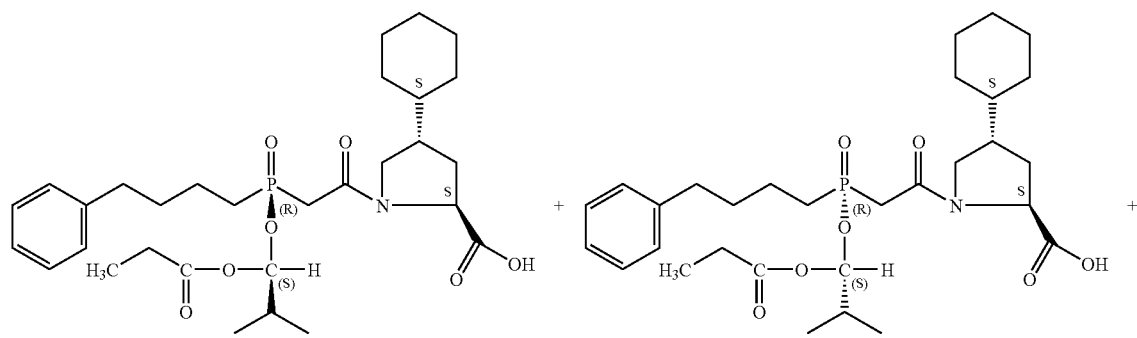

(II A) + (II B) +

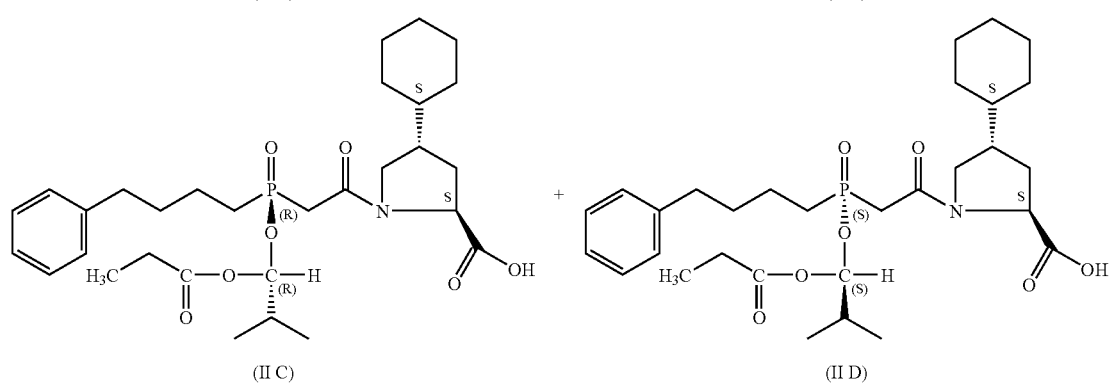

(II C) + (II D)

i. mixing with a cesium salt in presence of a solvent
ii. crystallisation of the mixture of cesium salts from the same solvent or mixture of solvents containing 1–10 moles of water

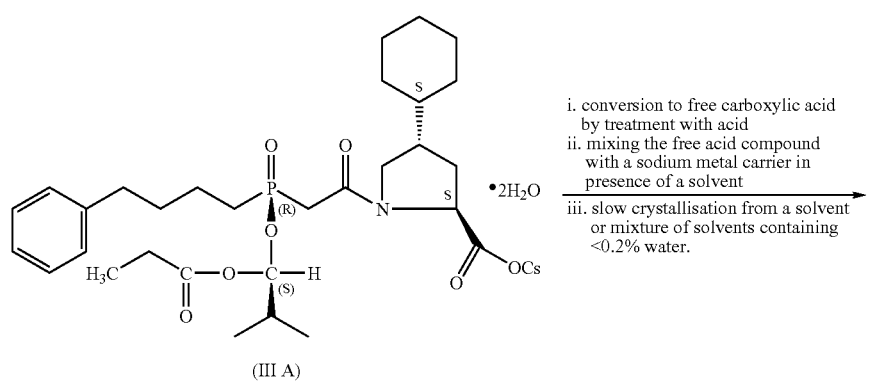

(III A)

i. conversion to free carboxylic acid by treatment with acid
ii. mixing the free acid compound with a sodium metal carrier in presence of a solvent
iii. slow crystallisation from a solvent or mixture of solvents containing <0.2% water.

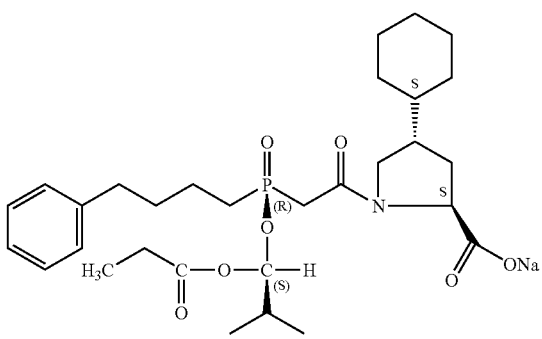

(I): Fosinopril Sodium Polymorphic Form-A

BRIEF DESCRIPTION OF THE FIGURES

FIG. 1 shows the 1R spectrum of the compound (III A).

FIG. 2 shows the X-ray (powder) diffraction pattern of the compound (III A).

FIG. 3 shows the DSC of the compound (III A).

FIG. 4 shows the TG thermogram of the compound (III A).

DETAILED DESCRIPTION OF THE INVENTION

Fosinopril, viz. 1[{2-Methyl-1-(1-Oxopropoxy)propoxy)-4-phenylbutyl}acetyl](trans)-4-cyclohexyl-L-Proline of formula (II) has four centres of asymmetry in the molecule. Two such centres are present in the proline fragment of the compound i.e. at 4-position of the proline ring to which the cyclohexyl group is attached and at 2-position of the proline ring carrying the carboxylic acid function. The third centre is on the carbon atom number 12, which is attached to the phosphorous atom through oxygen linkage. The last one is on the phosphorous atom, which arises due to racemisation when the isobutylpropionate group is attached to it.

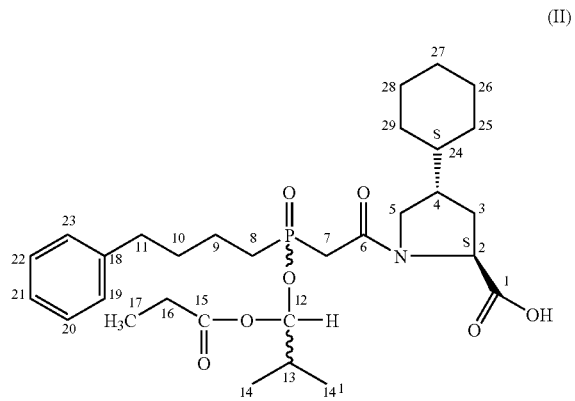

(II)

Because of the four asymmetric centres present in the molecule, compound of formula (II) would give rise to sixteen isomers. Out of these, only one isomer is a therapeutic. As evident from prior art, the methods described in U.S. Pat. No. 4,337,201 probably lead to a synthesis of fosinopril, probably obtained as a mixture of all possible sixteen isomers or as a mixture of some of the possible isomers.

Further, U.S. Pat. No. 4,337,201 neither suggests a method to separate the desired isomer of therapeutic value from the mixture of other unwanted isomers nor a method for synthesis of the product containing predominantly the required isomer.

Thus, to summarise, practise of the chemistry embodied in U.S. Pat. No. 4,337,201, comprising of reacting a compound of formula (4) with a haloester of formula (5) to give compound of formula (3) wherein when $R^1$, $R^2$, $R^3$, $R^{4a}$, $R^4$, $R^5$, n and X are phenylbutyl, isobutylpropionate, hydrogen, alkyl or aralkyl, hydrogen, 4-cyclohexyl-proline, zero and halogen respectively would give fosinopril of formula (II) as a mixture of all possible sixteen isomers or as a mixture of some of the possible isomers. Separation of the isomers would be very tedious and if achieved, it would not constitute a practical viable method for synthesis of fosinopril

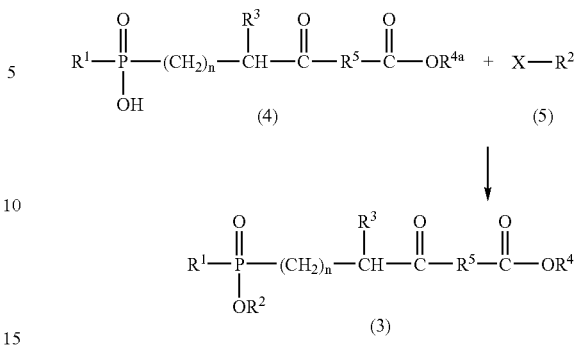

Synthesis of Fosinopril as a Single Desired Isomer of High Purity:

In the present invention this has been achieved in two steps i.e.

a) preparation of fosinopril as a mixture of four diastereomers and b) separation of the desired isomer from the mixture through formation of alkali metal salts followed by crystallisation.

The process for preparation of fosinopril as a mixture of four diastereomers is accomplished as summarised in Scheme-II by (i) Reacting a phosphinyl acetic acid derivative of formula (IV), wherein $R^7$ is lower alkyl of 1–4 carbon atoms with (trans)-4-cyclohexyl-L-proline derivative of formula (V), in which the carbon atoms at position no. 2 carrying the carboxylic acid group and position no. 4 to which the cyclohexyl group is attached are both in the (S)-configuration and $R^8$ is a group easily removable by hydrogenolysis and is preferably benzyl or benzyl substituted at ortho, meta or para positions by an alkyl, alkoxy, alkanoyl, phenyl, nitro or a dialkylamino group, followed by removal of the protective group $R^7$ by conventional means to give the phosphinyl acetamido proline derivative of formula (VI), wherein $R^7$ is hydrogen and $R^8$ has the same meaning as mentioned hereinbefore The reaction, which essentially involves formation of an amide bond, can be accomplished in a number of ways as reported in the literature. For example, the reaction can be carried out by coupling of compound of formula (IV) and (V) in the presence of coupling agents such as dicyclohexylcarbodiimide or the compound of formula (IV) can be reacted with compound of formula (V), after activation of the carboxylic acid function by formation of its mixed anhydride, symmetrical anhydride, acid halide and acid ester.

Preferably, in the present invention the amide bond formation is achieved by reacting compound of formula (IV) with compound of formula (V), the carboxylic acid function of which is activated by formation of its mixed anhydride with pivaloyl chloride, in the presence of a base and a solvent, to give compound of formula (VI), wherein $R^7$ is lower alkyl of 1–4 carbon atoms.

The reaction can be carried out in a solvent selected from acetonitrile, dichloromethane, dichloroethane, dioxane, N,N-dimethylacetamide, N,N-dimethylformamide and tetrahydrofuran, or mixtures thereof. An amount of solvent sufficient enough to dissolve the reactants is adequate.

Organic bases such as triethylamine, tripropylamine, pyridine, DBU and N-methyl morpholine can be used for the reaction. The bases can be employed in a molar ratio to compound of formula (IV) of within the range from about 1:3, preferably from about 1:1.5 to about 1:2.

Normally, about one molar equivalent or a slight excess of the mixed anhydride with respect to compound (V) is sufficient for activation of the carboxylic acid function The reaction can be carried out at temperatures ranging from −60 to +30° C., preferably at a temperature ranging between −40 to 15° C.

In a preferred embodiment, a solution of compound (IV), wherein $R^7$ is methyl or ethyl in a solvent, preferably acetonitrile, dichloromethane or tetrahydrofuran, and containing the organic base is reacted with pivaloyl chloride at a temperature ranging from −60 to −10° C. for about 0.5 to 1.0 hours. To this solution is added a solution of (trans)-4-cyclohexyl-L-proline (V) in a solvent selected from acetonitrile, dichloromethane or tetrahydrofuran at the same temperature and allowed to react for 1 to 2 hrs at a temperature ranging from −40 to 15° C. At the end of the reaction water is added to the reaction mixture and the aqueous phase extracted with ethyl acetate. Evaporation of ethyl acetate gives compound (VI), wherein $R^7$ is lower alkyl of 1–4 carbon atoms.

(ii) Removal of the alkyl protective group $R^7$ in compound of formula (VI) to give compound of formula (VI) in which the group $R^7$ is hydrogen. This can be achieved by standard methods known in the art for hydrolysis of alkoxy esters. One such method consists of reacting compound of formula (VI) in which $R^7$ is lower alkyl of 1–4 carbon atoms with a silyl compound or a mixture of silyl compounds optionally in the presence of an alkali metal halide in presence of a solvent as per the methods described in *Synthesis*, 219 (1982) and Example 48 of U.S. Pat. No. 4,337,201.

Preferably, the deprotection is carried out by reacting compound of formula (VI), in which $R^7$ is lower alkyl of 1–4 carbon atoms with a silyl compound or a mixture selected from trimethyl chlorosilane, trimethylbromosilane and hexadimethylsilazane and in presence of an alkali metal halide, such as sodium bromide and sodium iodide in an organic solvent selected from acetonitrile, dichloromethane, dichloroethane, dioxane, N,N-dimethylacetamide, N,N-dimethylacetamide, tetrahydrofuran, toluene and xylene at a temperature ranging from 0 to 110° C. for 1 to 2 hrs. At the end of the reaction, the hydroxy compound (VI) thus obtained is isolated by conventional methods.

The silyl compound can be employed in a molar ratio to compound of formula (VI), wherein $R^7$ is lower alkyl of within the range from about 1:3, preferably from about 1:1.5 to about 1:2. Similarly, the alkali metal halide can be employed in a molar ratio to compound of formula (VI), wherein $R^7$ is lower alkyl of within the range from about 1:3, preferably from about 1:1.5 to about 1:2.

The optical integrity of the proline fragment is maintained during the amide formation reaction i.e. both carbon atoms at position no. 2 and 4 of the proline ring retain the (S)-configuration in compound of formula (VI), wherein $R^7$ is lower alkyl or hydrogen.

(iii) Alkylation of compound of formula (VI) by reacting it with a halo ester of structure (VI) wherein X is halogen selected from chlorine, bromine and iodine in presence of an organic solvent and a base for 2 to 5 hrs at a temperature ranging from about 0 to 100° C. to give the phosphinylalkanoyl ester (II$^a$), wherein $R^8$ has the same meaning as defined earlier.

The phosphinic acid ester (VI), wherein $R^7$ is hydrogen can be employed in a molar ratio to the halo ester (VII) of within the range of about 1:4, preferably from about 1:1.5 to about 1:2. The solvents in which the reaction can be carried out include acetonitrile, dichloromethane, dichloroethane, ethylacetate, N,N-dimethylacetamide, N,N-dimethyl formamide, tetrahydrofuran, toluene, xylene.

Dichloromethane, ethyl acetate, toluene are xylene preferred solvents.

The organic bases that can be employed include triethylamine, tripropylamine, pyridine, DBU and N-methyl morpholine, with triethylamine preferred. The bases can be employed in a molar ratio to the hydroxy compound (VI), wherein $R^7$ is hydrogen of within the range of about 1:4, preferably from about 1:1.5 to about 1:2. The reaction is preferably carried out a temperature ranging from 5 to 25° C.

The compound (II$^a$) can be isolated from the reaction mixture by standard methods and subjected to deprotection of the group $R^8$. Alternatively, a solution of compound of formula (II$^a$) in an organic solvent obtained after work-up of the reaction ran without isolation of the compound be used for the deprotection.

(iv) Compound of formula (II$^a$), obtained as an oil or a solution of the same without isolation from the previous step is subjected to hydrogenolysis for removal of the carboxylic acid protective group $R^8$ by treatment with hydrogen in the presence of a hydrogenation catalyst, such as palladium on charcoal, or other conventional palladium catalysts in presence of a solvent to give fosinopril of formula (II) obtained as an oil after isolation.

The reaction can be carried out in a solvent selected from acetonitrile, ethanol, ethyl acetate, methanol, N,N-dimethyl acetamide, N,N-dimethyl formamide, tetrahydrofuran, toluene and xylene with, ethanol, ethyl acetate toluene and xylene preferred.

Out of the sixteen possible isomers, compound (II) of the present invention is obtained as a mixture of four isomers only, since carbon atoms no. 2 and 4, carrying the carboxylic acid and cyclohexyl group, respectively have a definite configuration i.e. both have the (S)-configuration. There are two other chiral centres in the molecule and each has its own configuration, classified as (R)- or (S)-. This in turn, gives rise to four isomers, since the first centre may be (R)- or (S)- and so may be the second.

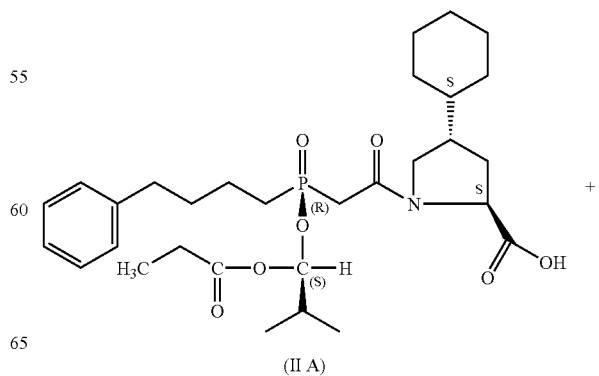

(II A)

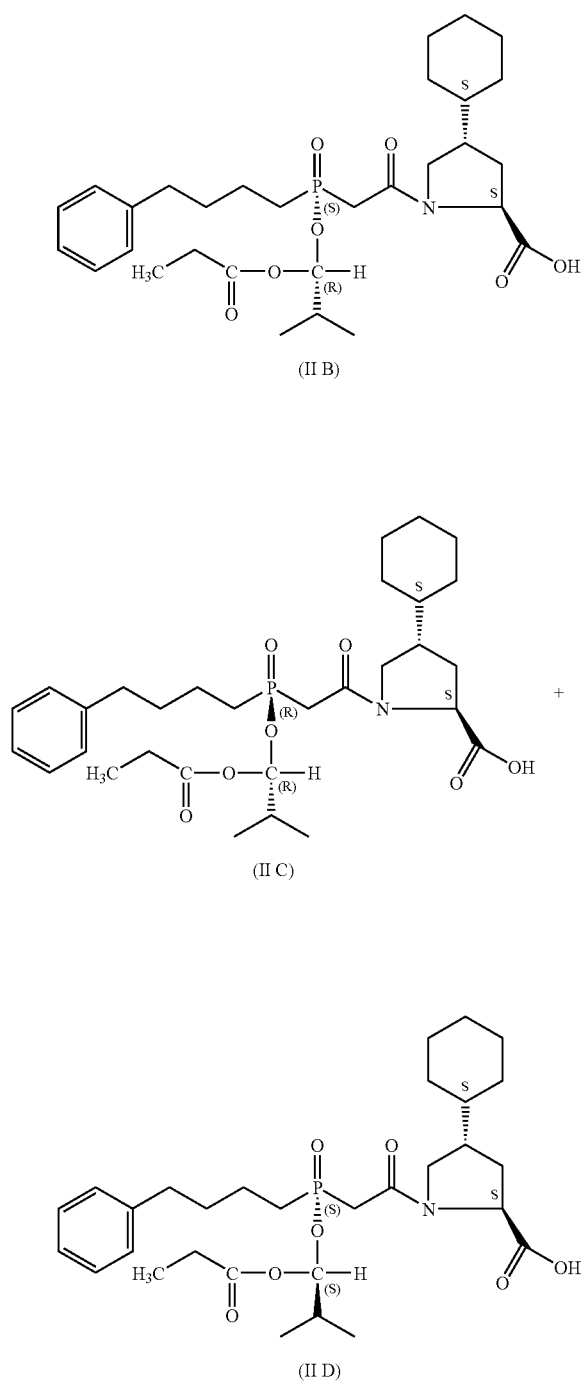

(II B)

(II C)

(II D)

Thus, the four isomers formed at the two chiral centres for compound (II) can be classified as, a) one in which the Phosphorous-oxygen linkage has the (R)-configuration and the C(12)–C(13) linkage has the (S)-configuration i.e. compound of formula II A (SRSS-configuration), b) one in which the Phosphorous-oxygen linkage has the (S)-configuration and the C(12)–C(13) linkage has the (R)-configuration i.e. compound of formula II B (RSSS-configuration), c) one in which the Phosphorous-oxygen linkage has the (R)-configuration and the C(12)–C(13) linkage has the (S)-configuration i.e. compound of formula II C (RRSS-configuration) and d) one in which the Phosphorous-oxygen linkage has the (S)-configuration and the C(12)–C(13) linkage has the (S)-configuration i.e. compound of formula II D (SSSS-configuration).

The starting compounds utilised in the invention, viz. compounds of formula (IV) and (V) are obtained by methods known in the art.

These four isomers A, B, C and D are not mirror images of each other i.e. they are diastereomers and not enantiomers. Diastereomers differ in their physical and chemical properties, solubilities and reactivity.

This is specially so when stereoelectronic factors control the course of reaction.

This aspect, specially the difference in solubility behaviour of diastereomers is used to advantage in the present invention to separate the desired isomer of fosinopril (II A) from a mixture of four diastereomers (II A), (II B), (II C) and (II D). The solubility profile of the individual diastereomers in the mixture in various solvents is not very different, but, however, becomes more pronounced when they are converted to a salt, specially salts with alkali metals and amines.

In general, the formation of alkali metal salts can be achieved by mixing together the mixture of four diastereomers in a suitable solvent with an alkali metal carrier for one to four hours. Solvents in which the diastereomeric mixture of compounds is soluble can be used. These include, acetone, acetonitrile, dichloromethane, dichloroethane, dioxane, ethyl acetate, methyl ethyl ketone, methyl isobutyl ketone, N,N-dimethyl acetamide, N,N-dimethyl formamide, tetrahydrofuran, toluene and xylene.

The alkali metals can be selected from sodium, potassium and cesium. The alkali metal carriers that can be employed are those commonly used for the alkali metal exchange and include carbonates, hydrogen carbonates and ethyl hexanoates of the respective alkali metals.

The alkali metal exchange can be accomplished under anhydrous or near anhydrous conditions in the absence of water when alkali metals salts of ethyl hexanoate is used. Water as present in the solvents employed is the only source of water. When alkali metal carbonates and alkali metal hydrogen carbonates are used water as required to dissolve the salts is necessary for the exchange.

The reaction can be carried from about −50 to 50° C., preferably from about −20 to 20° C.

The alkali metal carrier can be employed in a molar ratio to the diastereomeric mixture of compounds (II A), (II B), (II C) and (II D) of within the range of from about 1 to 3, preferably in the range of about 1 to 1.5

In a preferred aspect of the invention the separation of the desired isomer (II A) from the mixture of four diastereomers (IIA), (II B), (II C) and (II D) can be achieved in one step as summarised in Scheme-III by formation of the cesium salt, followed by crystallisation.

Accordingly, the mixture of diastereomers is mixed with a cesium salt in a suitable solvent mentioned earlier. Upon crystallisation from a suitable solvent or a mixture of solvents the cesium salt of the diastereomer (II A) separates out in a highly pure form.

Although, other alkali metal salts can be prepared, cesium alone is the most specific and the most preferred salt since it achieves clear separation of the desired diastereomer in one single crystallisation.

The crystallisation of the cesium salt is preferably carried out in solvents selected from acetone, acetonitrile, dichloromethane, diisopropyl ether, ethyl acetate and tertiary butyl methyl ether or mixtures thereof having a water content in the range of about 1 to 10 moles of the cesium salt of compound (II A)/(II B)/(II C)/(II D). Preferably, when water is in the range of about 2 to 5 moles the cesium salt of diastereomer (II A) crystallises out smoothly as the fosinopril cesium salt dihydrate of formula (III A).

When amount of water is below the preferred molar range, the compound (III A) does not crystallise out properly and tends to stick. When amount of water is higher than the preferred range considerable amount of compound (III A) is lost to the mother liquor during filtration of the product.

The fosinopril cesium salt dihydrate (III A) is isolated by filtration and is obtained in high purity, of ranging from about 99.2 to 99.5%. The product has distinct IR spectrum, $^1$H NMR spectrum and X-ray (powder) diffraction pattern, which are different from that reported for fosinopril sodium. The TG thermogram of the product confirms that it contains two molecules of water i.e. it is a dihydrate.

The IR spectrum, X-ray (powder) diffraction pattern, DSC and TG thermograms of compound (III A) are reproduced in FIG. 1, FIG. 2, FIG. 3 and FIG. 4 respectively.

Alternatively, the separation can be achieved in multiple steps. In the first step, alkali metal salts of the mixture of four diastereomers (II A), (II B), (II C) and (II D with sodium and potassium are prepared and allowed to crystallise from any of the solvent mentioned hereinearlier, preferably from acetone, acetonitrile, dichloromethane and ethyl acetate or a mixture of these solvents with diethyl ether and diisopropyl ether. A mixture predominantly containing two of the diastereomers (II A) and (II C) as their alkali metal salts, viz. (II A-ALKALI METAL SALT) and (II C-ALKALI METAL SALT), wherein the alkali metal salt is sodium or potassium separate out, which can be isolated by filtration and dried. Among the alkali metals, sodium is the most preferred, which separates the mixture of diastereomers (II A) and (II C) obtained in a ratio of 0.53:0.47. The chemistry employed is summarised in Scheme-VI.

The mixture of two diastereomeric alkali metal salts (II A-ALKALI METAL SALT) and (II C-ALKALI METAL SALT) can be further converted to the corresponding free acid mixture of diasteroemers (II A) and (II C) by treatment with an acid. Both inorganic and organic acids can be used to effect the hydrolysis.

Preferably, the alkali metal hydrolysis is effected by mixing a solution of the mixture of two diastereomers (II A-ALKALI METAL SALT) and (II C-ALKALI METAL SALT) in a solvent selected from dichloromethane, dichloroethane, diethyl ether, diisopropyl ether, ethyl acetate, methyl ethyl ketone, methyl isobutyl ketone, N,N-dimethyl acetamide, N,N-dimethyl formamide, tetrahydrofuran, toluene and xylene with a solution of potassium hydrogen sulfate in water at a temperature ranging from 5 to 35° C. at acidic pH in the range of about 1.0 to 4.0, preferably in the range of about 2.0 to 2.5. Evaporation of the solvent gives the mixture of two diastereomers (II A) and (II C) as an oil.

Further separation of mixture of two diastereomers (II A) and (II C) can be accomplished in two ways as summarised in Scheme-VII.

In one of the ways, the mixture of two diastereomeric free acids (II A) and (II C) can be mixed with an alkali metal salt in the presence of a solvent to form the corresponding alkali metal salt, from which the two diastereomers can be separated by preferential crystallisation of one diastereomer. The alkali metal salts that can be used include sodium, potassium and cesium. Among these again cesium is the most specific and the most preferred salt since it achieves clear separation of the two diastereomers.

In the other method, the mixture of two diastereomers (II A) and (II C) can be reacted with an amino compound in an organic solvent to form the corresponding amine salt. The amino compounds that can be used for forming the salt are selected from 2-amino-2-methyl-1-propanol, (+)-D-2-amino butanol, nicotinamide, dicyclohexyl amine and 1-adamantanamine, with 2-amino-2-methyl-1-propanol preferred. The salt formation can be carried out in a solvent selected from acetonitrile, diisopropyl ether, ethyl acetate and isopropyl acetate, at a temperature ranging from about −30 to +30° C.

Scheme-VI: Separation of diastereomers (II A), (II B), (II C) and (II D) as their sodium and potassium salts

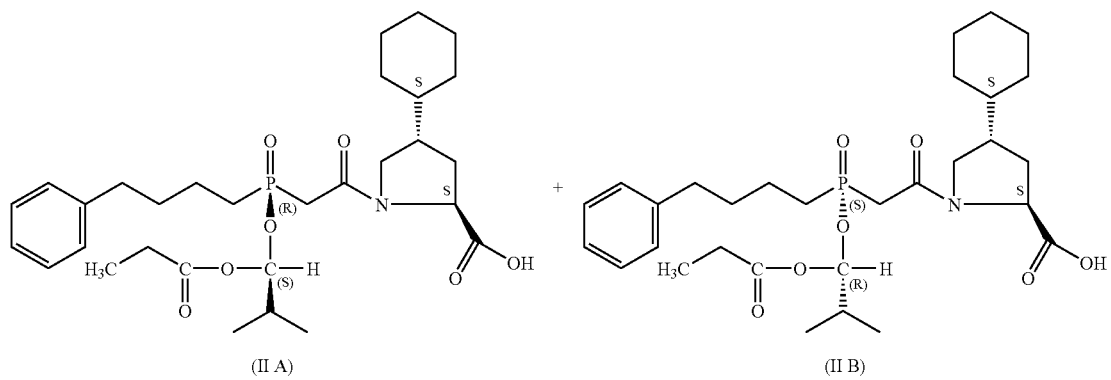

(II A)          (II B)

-continued

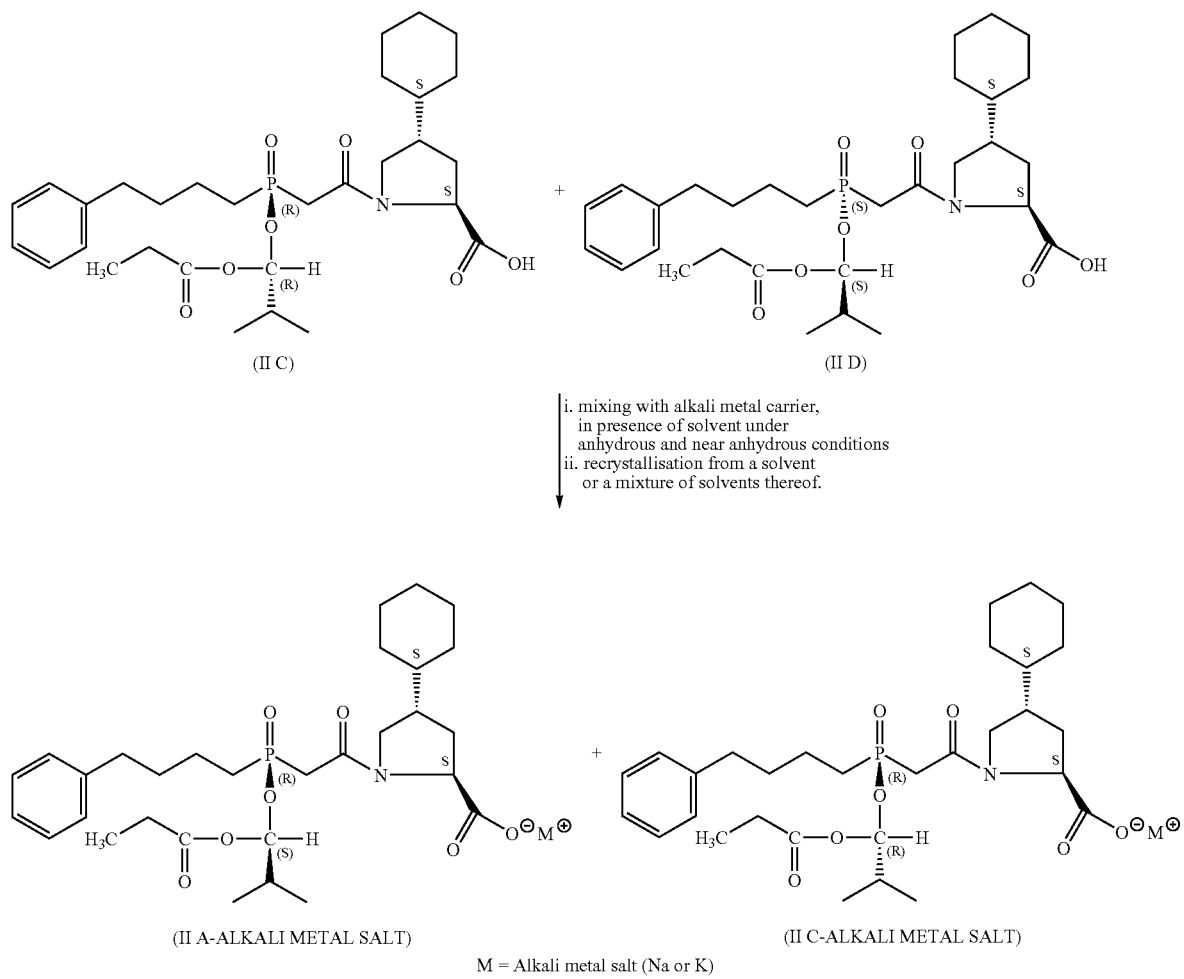

(II C) + (II D)

i. mixing with alkali metal carrier, in presence of solvent under anhydrous and near anhydrous conditions
ii. recrystallisation from a solvent or a mixture of solvents thereof.

(II A-ALKALI METAL SALT) + (II C-ALKALI METAL SALT)

M = Alkali metal salt (Na or K)

Scheme-VII: Separation of the four diastereomers via alkali metal and amine salts

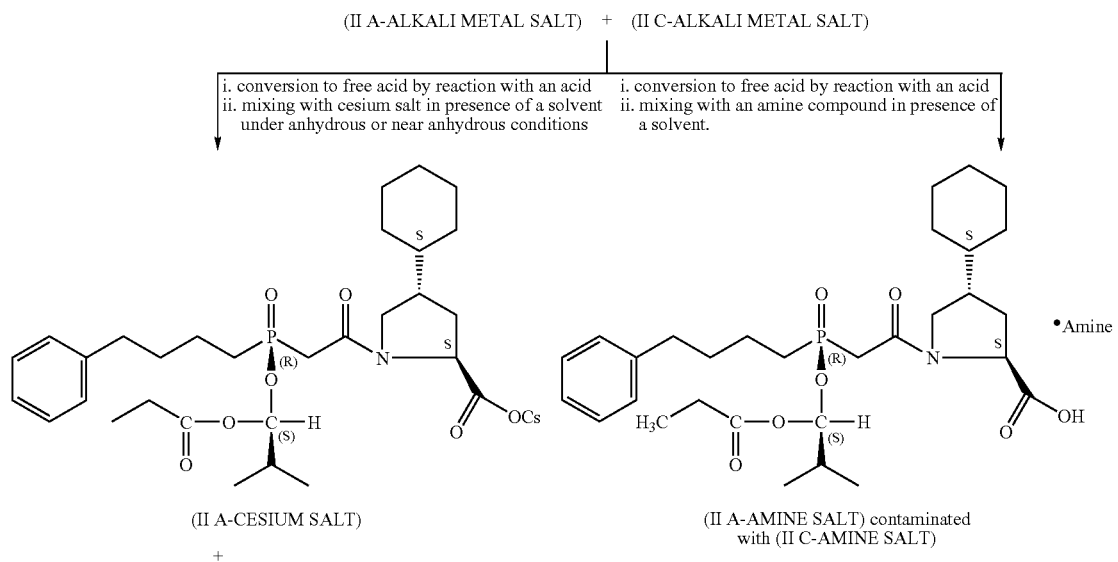

(II A-ALKALI METAL SALT) + (II C-ALKALI METAL SALT)

i. conversion to free acid by reaction with an acid
ii. mixing with cesium salt in presence of a solvent under anhydrous or near anhydrous conditions i. conversion to free acid by reaction with an acid
ii. mixing with an amine compound in presence of a solvent.

(II A-CESIUM SALT)
+

(II A-AMINE SALT) contaminated with (II C-AMINE SALT)

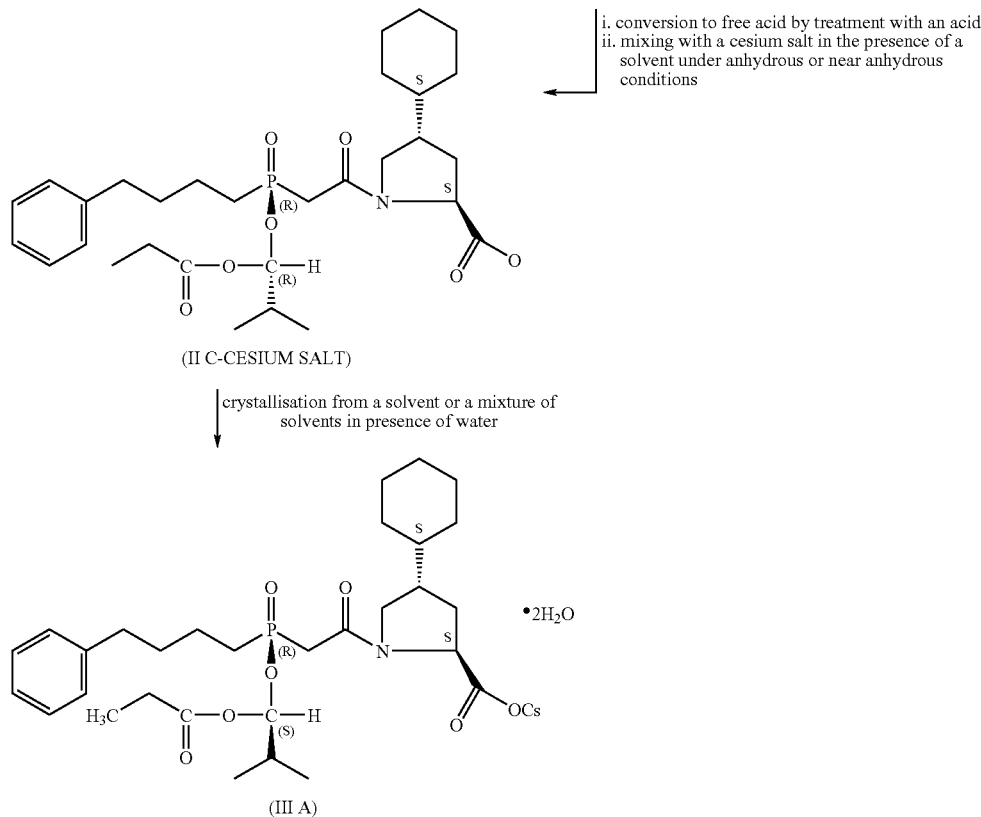

(II C-CESIUM SALT)

crystallisation from a solvent or a mixture of solvents in presence of water (III A)

Crystallisation of the amine salt thus obtained, from the same solvent used for salt formation or a mixture with a co-solvent affords a solid compound predominantly containing the unwanted diastereomer (II C), which is isolated by filtration. The mother liquor contains the desired diastereomer (II A) contaminated with about 10% of diastereomer (II C). Further upgradation of the product recovered from the mother liquor can be accomplished by reacting the product mixture with a cesium salt as described hereinearlier, followed by crystallisation to give compound (III A) in high purity.

All the methods summarised in Schemes-III, VI and VII can be employed for achieving the separation. The single step separation summarised in is most preferred even though, more amounts of the expensive cesium salt needs to be used rendering the process bit more costly than the others given in Scheme-VI and VII, which, however, are more cumbersome requiring multiple steps.

Compound of formula (III A), viz. [1[S*(R*),2α,4β]-4-cyclohexyl-1-[[[2-methyl-1-(1-oxopropoxy)propoxy)-4-phenylbutyl)phosphinyl]acetyl](trans)-4-cyclohexyl-L-proline, mono-cesium salt dihydrate is a novel crystalline compound having distinct X-ray (powder) diffraction pattern and is particularly a useful intermediate for synthesis of fosinopril sodium of high purity as would be evident from the method(s) described hereinbelow.

Preparation of Fosinopril Sodium (I) in Polymorphic Form-A from Fosinopril Cesium Salt Dihydrate (III A):

As summarised in Scheme-IV, the cesium salt (III A) is converted to the free acid by treatment with a strong acid in a similar manner as described earlier.

The free acid, i.e. fosinopril isomer (II A), is dissolved in an organic solvent selected from acetone, acetonitrile, dichloromethane, dichloroethane, diethyl ether, diisopropyl ether, dioxane, ethyl acetate, methyl ethyl ketone, methyl isobutyl ketone, N,N-dimethyl acetamide, N,N-dimethyl formamide, tetrahydrofuran, toluene and xylene, with dichloromethane and ethyl acetate preferred and can be mixed with a sodium metal carrier, selected from sodium ethyl hexanoate, sodium carbonate and sodium hydrogen carbonate for 1 to 4 hours, preferably 2 hours at a temperature ranging from 5 to 35° C. to form the sodium salt i.e. fosinopril sodium of formula (I).

When sodium ethyl hexanoate is employed as the sodium metal carrier, no water need to be added to the reaction mixture. The reaction can be carried out under anhydrous or near anhydrous conditions. Water, however, may be present as normally associated with the solvent(s) employed. The water content present is normally below 0.2%.

Preferably, the water content is in the range of 0.03 to 0.05% of the total solvent(s).

When sodium hydrogen carbonate or sodium carbonate is employed as the sodium salt, then the reaction system is biphasic, one is a solvent phase containing the dissolved fosinopril free acid is mer (II A) and the other is the aqueous phase in which the alkali metal salt is dissolved. In 1 to 4 hours the exchange is completed, after which the organic phase containing the sodium salt can be separated from the aqueous phase. The solution of fosinopril sodium in the organic solvent after separation usually has a water content in the range from about 1 to 2%.

The fosinopril sodium thus formed can be isolated by standard methods from the reaction mixture or preferably, without isolation can be crystallised from the same solvent or a mixture of solvents to give the polymorphic Form-A of the sodium salt.

The crystallisation is accomplished by agitating a solution of fosinopril sodium in any one of the solvents mentioned earlier or from the preferred solvents i.e. dichloromethane or ethyl acetate or a mixture thereof over a long of period of time of about 10 to 24 hours, preferably 10 to 15 hours for polymorphic Form-A to crystallise out, which can be isolated by filtration.

When the sodium salt is not isolated and the solution containing the same obtained by exchange with sodium ethyl hexanoate, either alone or mixed with another solvent is allowed to crystallise, the water content in the solvent is normally below 0.2%, more precisely in the range of about 0.03 to 0.05%. When the solution containing fosinopril sodium obtained by exchange with sodium carbonate or bicarbonate, either alone or co-mixed with another solvent is allowed to crystallise, the water content in the solvent is normally in the range of 1–2%. Slow crystallisation gives the polymorphic Form-A.

Alternatively, water can be azeotropically removed from the solution and brought down to a level of 0.03 to 0.05% and then allowed to set for crystallisation to give again the polymorphic Form-A.

The rate of crystallisation is the determining factor for formation of the polymorphic Form-A and not the solvent used or the water content present in the solvent.

When insufficient time is given for crystallisation the crystalline form obtained is found to be contaminated with other polymorphic form i.e. Form-B.

The product obtained on slow crystallisation by employing the above methods i.e. from a solution containing water in the range of 0.03 to 0.05% and from a solution containing water in the range from 1 to 2% have identical IR Spectrum, solid state $^{31}P$ and $^{13}C$ NMR specta and X-ray (powder) diffraction pattern, and conform to that reported for Fosinopril Sodium polymorph-A in the literature.

The polymorphic Form-A can be isolated by filtration from the solvent or solvent mixture from which it is crystallised and dried and has a purity >99%.

Conversion of Unwanted Isomers of Fosinopril Back to Fosinopril Sodium Polymorphic Form-A A further object and aspect of the present invention is to provide a method wherein the unwanted diasatereomers formed and separated in the processes mentioned herein earlier are converted back to fosinopril sodium (I) as the polymorphic Form-A as summarised in Scheme-V.

The method comprises of first pooling together all the unwanted diastereomers i.e. (II B), (II C) and (II D) contaminated with the diastereomer (II A) and their alkali metal salts thereof from the waste stream and subjecting the pooled mixture to hydrolysis to effect cleavage of the isobutyl propionate ester function attached to the phosphorous atom to give compound of formula (VIII)

The hydrolysis can be effected with a base or an acid. Moreover, the same can be accomplished using a combination of trimethylchlorosilane and an alkali metal halide like sodium iodide. Basic hydrolysis is preferred since it is accompanied by minimum impurity formation facilitating easy isolation of the product as a solid. The hydrolysis can be effected at a temperature ranging from about −10 to 80° C.

The carboxylic acid function on the proline ring is then selectively esterified to give an ester of formula (VI), wherein $R^7$ is hydrogen and $R^8$ is a group easily removable by hydrogenolysis, and is preferably benzyl or p-nitro benzyl group.

The esterification can be carried out by mixing together compound (VIII) in presence of a solvent and benzyl alcohol or p-nitro benzyl alcohol in presence of an acid or a base.

The acidic esterification is accomplished by heating together compound (VIII) and benzyl alcohol or p-nitro benzyl alcohol and an acid selected from p-toluene sulfonic acid and sulphuric acid in a hydrocarbon solvent selected from cyclohexane, benzene and toluene at reflux temperature of the solvent for 10–15 hrs. The preferred solvent and acid are cyclohexane and p-toluenesulfonic acid respectively. The acid can be employed in a ratio of 0.1 to 0.5 by weight of compound (VIII), preferably in the range of 0.1 to 0.25.

The basic esterification is accomplished by agitating together compound (VIII) and benzyl bromide or p-nitro benzyl bromide and a base selected from triethylamine, potassium carbonate, sodium carbonate and N-methyl morpholine in presence of a solvent selected from acetone and acetonitrile at a temperature ranging from about 25–80° C. for 5–10 hours.

The P—OH bond remains intact during the acidic and basic esterification. Compound (VI) can be isolated form the reaction mixture by conventional methods.

Compound (VI) is then alkylated with haloester of formula (VII) as per the method described hereinearlier and after removal of the protective group $R^8$ by hydrogenolysis fosinopril (II) is obtained as a mixture of four diastereomers (II A), (D B), (II C) and (II D).

Fosinopril cesium dihydrate (III A) can then be prepared from the mixture of diastereomers (II A), (II B), (II C) and (II D) by any of the methods summarised in Scheme-III, VI and VII, preferably Scheme-III. The compound (III A) is then converted to fosinopril sodium (I) in polymorphic Form-A as per the methods summarised in Scheme-IV.

The following examples represent the preferred embodiments of the invention, but however, should by no means be construed as limiting the scope of the invention.

EXAMPLE 1

1[{Methoxy(4-phenylbutyl)phosphinyl}acetyl]-(trans)-4-cyclohexyl-L-proline benzyl ester [Compound (VI), Wherein $R^7$ is Methyl]

(trans)-4-cyclohexyl-L-proline benzyl ester hydrochloride [(V), 100 gm, 0.309 moles) was taken in a mixture of dichloromethane (1050 ml) and water (468 ml) and cooled to 5–10° C. Aqueous ammonia solution (25%) was slowly added at the same temperature till the pH becomes 9.5–9.8. The organic phase was separated, washed with brine (200 ml) and concentrated. The residue was dissolved in tetrahydrofuran (300 ml) and the solution of (trans)-4-cyclohexyl-L-proline benzyl ester kept ready for the addition in the next phase.

[Methoxy(4-phenylbutyl)phosphinyl] acetic acid [(IV, $R^7$ is methyl), 98.2 gm, 0.363 moles) was dissolved in tetrahydrofuran (1000 ml) under nitrogen atmosphere and cooled to −20° C. N-methyl morpholine (55 gm, 0.544 moles) was added, followed by pivaloyl chloride (43.9 gm, 0.364 moles) at the same temperature. The reaction mixture was stirred for 0.5 hr and then cooled to −40° C. The solution of the (trans)-4-cyclohexyl-L-proline benzyl ester in tetrahydrofuran was added at the same temperature and stirred for 1 hr. The reaction mixture was concentrated and diluted with ethyl acetate (700 ml). To this was added 10% aqueous sodium bicarbonate solution (150 ml) and stirred for 10 mins. The organic phase was separated, washed with 1N HCl (200 ml), water (200 ml×2) and the solvent evaporated off to give 166.5 gm (quantitative) of the title compound as an oil.

IR (Neat): 2927.7, 2852.5, 1743.5, 1651.0, 1433.0, 1172.6 cm$^{-1}$ $^1$H NMR (CDCl$_3$): δ 7.4–7.1 (m, 10H, aromatic protons); 5.2–5.05 (m, 2H, —O—C$\underline{H}$2-Ph); 4.7–4.5 (d, 1H, J=9 Hz. —C$\underline{H}$—COOCH$_2$Ph); 4.0–3.85 (m, 1H); 3.8–3.65 (m, 3H, —OC$\underline{H}_3$); 3.4–2.5 (m, 5H, —P—C$\underline{H}_2$—CO—, Ph-C$\underline{H}_2$— and —N—C$\underline{H}$—); 2.25–1.5 (m, 14H); 1.3–0.8 (m, 6H)

EXAMPLE 2

1[{Hydroxy(4-phenylbutyl)phosphinyl}acetyl]-(trans)+cyclohexyl-L-proline benzyl ester [Compound (VI), Wherein R$^7$ is Hydrogen]

1[{Methoxy(4-phenylbutyl)phosphinyl}acetyl])-4-cyclohexyl-L-proline benzyl ester (VI), obtained in Example 1 (166.5 gm, 0.309 moles) was dissolved in acetonitrile (1750 ml) and cooled to 10–15° C. Sodium iodide (78.7 gm, 0.525 moles) and trimethyl silyl chloride (57 gm, 0.525 moles) were added to the solution and agitated at the same temperature for 1.5 hrs. A 33% aqueous sodium carbonate solution was added to the reaction mixture and the pH adjusted to about 4.5. The solids were filtered and the filtrate was concentrated and the residue was dissolved in ethyl acetate (1165 ml) and stirred to get a clear solution. The ethyl acetate solution was washed with water (166 ml) and 5% aqueous sodium thiosulphate solution (166 ml). Water (166 ml) was added to the ethyl acetate portion and pH of the mixture was adjusted to 8.4–8.5 by adding 33% aqueous sodium carbonate solution. The organic portion was separated and mixed with water (166 ml). Conc. HCl was added to the mixture and the pH adjusted to 2.2–2.3. The organic phase was further separated and the solvent evaporated off to give 138 gm (85%) of the title product as an oil.

IR (Neat): 2925.8, 2852.5, 1743.5, 1645.2, J604.7, 1434.9, 1172.6, 960.5 cm$^{-1}$ $^1$H NMR (CDCl$_3$): δ 7.4–7.1 (m, 10H, aromatic protons); 5.25–5.05 (m, 2H, —OC$\underline{H}$2-Ph); 4.7–4.55 (d, 1H, J=9 Hz, —C$\underline{H}$—COOCH$_2$Ph); 4.0–3.8 (m, 1H, —N—C$\underline{H}$—); 3.3–3.15 (m, 1H, —N—C$\underline{H}$—); 3.0–2.5 (m, 4H, —P—C$\underline{H}_2$—C— and Ph-C$\underline{H}_2$—); 2.2–1.5 (m, 14H); 1.3–0.7 (m, 6H)

EXAMPLE 3

1[{2-Methyl-1-(1-oxopropoxy)propoxy)-4-phenylbutyl}acetyl]-(trans)-4-cyclohexyl-L-proline benzyl ester [Compound (II$^a$)]

1[{Hydroxy(4-phenylbutyl)phosphinyl}actyl]-(trans)-4-cyclohexyl-L-proline benzyl ester (VI), obtained in Example 2 (64 gm, 0.122 moles) was taken in toluene (400 ml) and triethylamine (21.5 gm, 0.213 moles) was added at 25° C. 1-Bromo isobutyl propionate [37 gm, 0.177 moles, Compound (VII)] was added and the reaction mixture was heated at 90–95° C. for 3 hrs and cooled to room temperature. Water (150 ml) was added and stirred for 20 mins. The organic phase was separated, washed with 0.1N HCl (100 ml), dried over anhydrous magnesium sulfate and the solvent evaporated off to give 71.6 gm (90%) of the title product as an oil.

IR (Neat): 2925.8, 2852.5, 1747.4, 1651.0, 1434.9, 1174.6 cm$^{-1}$ $^1$H NMR (CDCl$_3$): δ 7.3–7.0 (m, 10H, aromatic protons); 6.3–6.1(m, 1H, O—C$\underline{H}$—O); 5.25–5.0 (m, 2H, —O—C$\underline{H}$2-Ph); 4.6–4.45 (m, 1H, —C$\underline{H}$—COOCH$_2$Ph); 4.1–3.6 (m, 1H); 3.45–2.65 (m, 3H, —P—C$\underline{H}_2$—CO—, —N—C$\underline{H}$—); 2.6–2.5 (m, 2H, Ph-C$\underline{H}_2$); 2.4–2.15(m, 3H); 2.15–1.75(m, 5H); 1.75–1.45 (m, 9H); 1.3–0.7 (m, 15H)

EXAMPLE 4

1[{2-Methyl-1-(1-oxopropoxy)propoxy)-4-phenylbutyl}acetyl]-(trans)-4-cyclohexyl-L-proline [Compound (II) as a mixture of four diastereomers (II A), (II B), (II C) and (II D)]

1[{2-Methyl-1-(1-oxopropoxy)propoxy)-4-phenylbutyl}acetyl]-(trans)-4-cyclohexyl-L-proline benzyl ester [(II$^a$, obtained in Example 3) 79.6 m 0.122 moles) was taken in toluene (240 ml) and transferred to a parr bottle and mixed with 10% Pd/C (8 gm) added and the reaction mixture stirred under 65–70 psi of Hydrogen gas pressure for 1.5 hrs. The palladium catalyst was filtered and the filtrate concentrated to give 68.6 gm (quantitative) of the title compound mixture of four diastereomers as an oil.

IR (Neat): 2925.8, 1755.1, 1651.0, 1604.7, 1450.4, 1174.6 cm$^{-1}$ $^1$H NMR (CDCl$_3$): δ 7.25–7.0 (m, 51, aromatic protons); 6.3–6.1(m, 1H, O—C$\underline{H}$—O); 4.6–4.5 (m, 1H, —C$\underline{H}$—COOH); 4.05–3.7 (m, 2H); 3.5–2.7 (m, 3H); 2.6–2.5 (m, 2H, PhC$\underline{H}_2$); 2.5–2.25(m, 3H); 2.2–1.8(m,5H); 1.8–1.4 (m, 9H); 1.3–0.7 (m, 15H)

EXAMPLE 5

[{2-Methyl-1-(1-oxopropoxy)propoxy)-4-phenylbutyl}acetyl]-(trans)-4-cyclohexyl L-proline sodium salt [Mixture of Sodium Salt of Diastereomers (II A) and (II C)]

1[{2-Methyl-1-(1-oxopropoxy)propoxy)-4-phenylbutyl}acetyl]-(trans)-4-cyclohexyl-L-proline [mixture of four diastereomers (II A), (II B), (II C) and (II D), obtained in Example 4, 68.7 gm, 0.122 moles] was dissolved in ethyl acetate (276 ml) and cooled to 10° C. 10% aqueous solution of sodium bicarbonate (123 ml, 0.1464 moles) was added and stirred for 2 hrs. The organic portion was separated and concentrated under reduced pressure. Diisopropyl ether (310 ml) was added to the residue and stirred for 6 hrs at 20° C. The solid which crystallises out was filtered and dried under vacuum to give 22 gm of a compound mixture of sodium salt f diastereomers (II A) and (II C) in a ratio of 0.53:0.47 as a white solid.

IR (KBr): 2925.8, 2856.4, 1757.0, 1624.0, 1600.8, 1452.3, 1409.9, 950.8 cm$^{-1}$ $^1$H NMR (CDCl$_3$): δ 7.3–7.05 (m, 5H, aromatic protons); 6.35–6.2(m, 1H, O—C$\underline{H}$—O); 4.5–4.35 (m, 1H, —C$\underline{H}$—COONa); 3.95–3.72 (m, 1H); 3.4–2.85 (m, 3H, —P—C$\underline{H}_2$—CO—, —N—C$\underline{H}$—); 2.7–2.55 (t, 2H, PhC$\underline{H}_2$); 2.5–2.25(m, 3H); 2.2–1.85(m, 5H); 1.8–1.5 (m, 9H); 1.4–0.8 (m, 15H)

EXAMPLE 6

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Mono Cesium Salt Dihydrate [Compound (III A)]: Via the Sodium Salt Mixture To a mixture of ethyl acetate (50 ml) and water (25 ml), the mixture of sodium salt of diastereomers (II A) and (II C), obtained in Example 5 (5 gm, 0.00854 moles) was added and cooled to 0–5° C. To this was added an aqueous solution of potassium hydrogen sulfate slowly till the pH is adjusted to 2.5. The organic phase was separated and the solvent evaporated off. Diisopropyl ether (35 ml) was added to the residue and stirred to get a clear solution. To this was added an aqueous solution of cesium carbonate (1.33 gm, 0.0041 moles in 0.6 ml water) at −10° C. and stirred for 2 hrs. The reaction mass was concentrated and the residue mixed with diisopropyl ether (75 ml) and stirred at −10° C. for another 2 hrs. The precipitated solids were filtered and the solid washed with diisopropyl ether (25 ml). After drying the solid was redissolved in dichloromethane (30 ml), mixed with diisopropyl ether (90 ml) and stirred for 1 hr. The solid product was filtered and washed with diisopropyl ether (30 ml) and dried to give 1.3 gm of the title compound as a white solid, having purity of 99.5%.

IR (KBr): 3278.8, 2922.0, 2850.6, 1739.7, 1633.6, 1589.2, 1461.9, 1396.4, 1215.1, 1186.1 cm$^{-1}$ $^1$H NMR (CD$_3$OD): δ 7.156.95 (m, 5H, aromatic protons); 6.15–6.05 (m, 1H, O—C$\underline{H}$—O); 4.28-4.2 (d, 1H, J=9 Hz, —C$\underline{H}$═COOCs); 3.75-3.6 (m, 1H, —NC$\underline{H}$—); 3.28-3.1 (m, 1H, —N—C$\underline{H}$—); 3.08-2.68(m, 2H, P—C$\underline{H_2}$—CO—); 2.58-2.4 (t, 2H, Ph-C$\underline{H_2}$); 2.35-2.15(m, 3H); 2.1-1.7(m, 5H); 1.7-1.35 (m, 9H); 1.25-0.65 (m, 15H)

EXAMPLE 7

[1[S*(R*)],2α,4β]-4-cyclohexyl-1-[[[2-methyl-1-(1-oxopropoxy)propoxy)-4-phenylbutyl]acetyl]-(trans)-4-cyclohexyl-L-proline Mono Cesium Salt Dihydrate [Compound (III A)]

Corresponding acid of the mixture of sodium salt of two diastereomers (II A) and (II C) [5 gm, 0.00854 moles] was prepared exactly as described in Example 6. Dichloromethane (25 ml) was added to the residue and stirred to get a clear solution. Cesium Carbonate (1.33 gm, 0.0041 moles) was dissolved in water (0.6 ml) and added to the solution at −10° C. and the mixture stirred for 2 hrs. The reaction mass was concentrated and the residue mixed with diisopropyl ether (75 ml) and stirred for another 2 hrs at −10° C. The precipitated solid was filtered and the solid washed with diisopropyl ether (25 ml). After drying the solid was redissolved in dichloromethane (30 ml), mixed with diisopropyl ether (90 ml) and stirred for 1 hr. The solid product was filtered and washed with diisopropyl ether (30 ml). It was dried to give 1.3 gm of the title compound as a white solid, having purity of 99.5%.

EXAMPLE 8

[1[(S*(R*)],2α,4β]-4-cyclohexyl-1-[[[2-methyl-1-(1-oxopropoxy)propoxy)-4-phenylbutyl]acetyl]-(trans)-4-cyclohexyl-L-proline Mono Cesium Salt Dihydrate [Compound (III A)]

Corresponding acid of the mixture of sodium salt of two diastereomers (II A) and (II C) [5 gm, 0.00854 moles] was prepared exactly as described in Example 6 Ethyl acetate (25 ml) was added to the residue and stirred to get a clear solution. Cesium Carbonate (1.33 gm, 0.0041 moles) was dissolved in water (0.6 ml) and added to the solution of the compound at −10° C. and the mixture stirred for 2 hrs. The reaction mass was concentrated and the residue was mixed with ethyl acetate (35 ml) and stirred at −10° C. for another 2 hrs. The crystallised solid was filtered, dried and redissolved in dichloromethane (30 ml), mixed with diisopropyl ether (90 ml) and stirred for 1 hr. The solid product was filtered and washed with diisopropyl ether (30 ml) and dried to give 1 gm of the title compound as white solid, having purity of 99.5%.

EXAMPLE 9

[1[S*(R*)],2α,4β]-4-cyclohexyl-1-[[[2-methyl-1-(1-oxopropoxy)propoxy)-4-phenylbutyl]acetyl]-(trans)-4-cyclohexyl-L-proline Mono Cesium Salt Dihydrate [Compound (III A)]

Cesium salt of the diastereomers (II A) and (II C) was prepared from their sodium salt (5 gm, 0.00854 moles) exactly as in Example 6. The dried solid was dissolved in dichloromethane (30 ml) to which ethyl acetate (90 ml) was added and the mixture stirred for 1 hr. The solid which crystallises out was filtered and dried to yield 1 gm of the title compound as a white solid, having purity of 99.5%.

EXAMPLE 10

[1[S*(R*)],2α, 4β]-4-cyclohexyl-1-[[[2-methyl-1-(1-oxopropoxy)propoxy)-4-phenylbutyl]acetyl-(cyclohexyl-L-proline Mono Cesium Salt Dihydrate [Compound (III A)]

Cesium salt of the diastereomers (II A) and (II C) was prepared from their sodium salt (5 gm, 0.00854 moles) exactly as in Example 6. The dried solid was dissolved in acetone (40 ml) at 40–45° C. and the solution cooled 20–25° C. and stirred for 1 hr. The solid which crystalises out product was filtered and dried to give. 1.1 gm of the title compound as a white solid, having purity of 99.5%.

EXAMPLE 11

[1[S*(R*)],2α,4β]-4-cyclohexyl-1-[[[2-methyl-1-(1-oxopropoxy)propoxy)-4-phenylbutyl]acetyl]-(trans)-4-cyclohexyl-L-proline Mono Cesium Salt Dihydrate [Compound (III A)]

Cesium salt of the diastereomers (II A) and (II C) was prepared from their sodium salt (5 gm, 0.00854 moles) exactly as in Example 6. The dried solid dissolved in acetonitrile (30 ml, water content 2%) at 40–45° C. and then further cooled 20–25° C. and stirred for 1 hr. The solid which crystallises out was filtered and dried to give 1.1 gm of the title compound as a white solid, having purity of 99.5%.

EXAMPLE 12

[1[S*(R*)],2α,4β]-4-cyclohexyl-1-[[[2-methyl-1-(1-oxopropoxy)propoxy)-4-phenylbutyl]acetyl]-(trans)-4-cyclohexyl-L-proline Mono Cesium Salt Dihydrate [Compound (III A)]: Via the Amine Salt Mixture Part A: 1[{2-Methyl-1-(1-oxopropoxy)propoxy)-4-phenylbutyl}acetyl]-(trans)-4-cyclohexyl-L-proline, 2-amino-2-methyl-1-propanol Salt (Mixture of 2-amino-2-methyl-1-propanol Salt of Diastereomers (II A) and (III C)]

To a mixture of ethyl acetate (50 ml) and water (25 ml), the mixture of sodium salt of diastereomers (II A) and (II C), obtained in Example 5 (5 gm, 0.00854 moles) was added and cooled to 0–5° C. To this was added an aqueous solution of potassium hydrogen sulfate slowly till the pH is adjusted to 2.5. The organic layer was separated, washed with water and brine and was cooled to 5° C. To the cooled solution was added 2-Amino-2-methyl-1-propanol (0.769 gm, 0.00863 moles) and stirred for 45 mins. The reaction mass was concentrated and diisopropyl ether (50 ml) was added to the residue and stirred for 1 hr at 0–5° C. The precipitated solid was filtered and washed with diisopropyl ether (20 ml) and dried. The dried solid was stirred with acetonitrile (40 ml) at 0–5° C. for 1 hr and filtered. The solid was washed with acetonitrile (20 ml). The solid amine salt was again stirred with ethyl acetate (20 ml, water content 1.5%) for 30 mins. Filtration gave 1 gm of solid, predominantly containing the 2-amino-2-methyl-1-propanol salt of diastereomer (II C).

The diisopropyl ether and acetonitrile mother liquors were combined and concentrated to give 2.5 gm of a residue consisting of a mixture of about 90% of the 2-amino-2-methyl-1-propanol salt of diastereomer (II A) and about 10% of the 2-amino-2-methyl-1-propanol salt of diastereomer (II C).

Part B: Preparation of Cesium Salt from the Amine Salt

The solid amine salt obtained from the combined mother portion in Part A consisting of a mixture of about 90% of the 2-amino-2-methyl-1-propanol salt of diastereomer (II A) and about 10% of the 2-amino-2-methyl-1-propanol salt of diastereomer (II C) was mixed with ethyl acetate (20 ml) and water (10 ml) and cooled to 0–5° C. To this was slowly added an aqueous solution of sodium hydrogen sulfate till pH of the reaction mixture is adjusted to 2.5. The organic phase was separated, washed with water, brine and the solvent evaporated off.

The residue is converted to the cesium salt as per any of the method described in Examples 6 to 11 to give the title compound (III A).

EXAMPLE 13

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Mono Cesium Salt Dihydrate [Compound (III A)]: Directly from the Mixture of Four Diastereomers To a solution of 2.4 gm (0.00426 moles) of the mixture of four diastereomers (II A), (II B), (II C) and (II D) in dichloromethane (24 ml) cooled to −20±2° C. was added a solution of 0.66 gm (0.0041 moles) of cesium carbonate in 0.26 ml of water and the mixture stirred at −20±2° C. for 4 hrs. The reaction mixture was concentrated and the residue was dissolved in diisopropyl ether (108 ml) and stirred at −10° C. for 2 hrs. The solid which crystallises out was filtered and washed with diisopropyl ether (15 ml) and dried. The dried solid (0.5 gm) is redissolved in dichloromethane (5 ml) and mixed with diisopropyl ether (15 ml) and stirred for 3 hrs. The solid which crystallises out was filtered, washed with diisopropyl ether and dried to give 0.4 gm of the title compound as a white solid, having purity of 99.5%.

EXAMPLE 14

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Sodium Salt Polymorph A [Compound (I)]

Fosinopril cesium, viz. [1[S*(R*)],2α,4β]-4-cyclohexyl-1-[[[2-methyl-1-(1-oxopropoxy)propoxy)-4-phenylbutyl}-acetyl]-(trans)-4-cyclohexyl-L-proline cesium salt dihydrate (III A) [20 gm, 0.0288 moles, obtained from any of the Examples 6–13] was taken in a mixture of dichloromethane (270 ml) and water (130 ml) and cooled to 0–5° C. To this was added an aqueous solution of potassium hydrogen sulfate slowly till the pH is adjusted to 2.5. The organic phase was separated and the solvent evaporated off. The residue was redissolved in dichloromethane (170 ml) and the solution was cooled to 10° C. and mixed with 10% aqueous solution of sodium bicarbonate (23 ml, 0.02735 moles) and stirred for 2 hrs. The organic phase was separated and water was azeotropically removed from the solvent till the water content becomes about 0.03%. To the solution was added ethyl acetate (250 ml) and the solution stirred for 15 hrs. The solid which crystallises out was filtered and washed with ethyl acetate (40 ml) and dried under vacuum at 40° C. for 6 hrs to give 14.5 gm (86%) of fosinopril sodium (I) as polymorphic Form-A as a white solid, having purity of 99.5%.

IR (KBr): 2924.9, 2856.2, 1759.3, 1622.6, 1600.2, 1452.1, 1409.1, 1384.6 cm$^{-1}$ $^1$H NMR (CD$_3$OD): δ 7.15–6.95 (m, 5H, aromatic protons); 6.15–6.05(m, 1H, O—C$\underline{H}$—O); 428–4.2 (d, 1H, J=9 Hz, —C$\underline{H}$—COONa); 3.75–3.6 (m, 1H, —NC$\underline{H}$—); 3.28–3.1 (m, 1H, —N—C$\underline{H}$—); 3.08–2.68(m, 2H, P—C$\underline{H_2}$—CO—); 2.58–2.4 (t, 2H, Ph-C$\underline{H_2}$); 2.35–2.15(m, 3H); 2.1–1.7(m,5H); 1.7–1.35 (m, 9H); 1.25–0.65 (m, 15H) 13C CP-MAS at 8 KHz: 173.3, 167.5, 160.1, 137.95, 120.6, 109.74, 103.98, 95.98, 74.32, 60.87, 60.46, 59.32, 56.78, 49.45, 47.8, 45.4, 38.8; 35.9, 32.5, 28.7, 23.5, 20.9, 20.1, 16.2, 15.08, 3.42 31 P HPDEC at 8 Kz: 53.355 [α]$_D$ at 23° C.−5.1(c=2,MeOH)

EXAMPLE 15

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Sodium Salt Polymorph A [Compound (I)]

Fosinopril acid was prepared from the cesium salt dihydrate [(III A), 1 gm, 0.00144 moles] exactly as described in Example 14. The residue was dissolved in dichloromethane (10 ml) and mixed with 10% aqueous solution of sodium bicarbonate (1.15 ml, 0.00136 moles) and stirred for 2 hrs. The organic phase was separated and water was azeotropically removed from the solvent till the water content becomes about 0.03%. The volume of the reaction mixture was brought down to ca. 5 ml and the solution was stirred for 15 hrs. The solid which crystallises out was filtered and dried under vacuum at 40° C. for 6 hrs to give 0.5 gm of the title compound as a white solid, having purity of 99.5%.

EXAMPLE 16

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Sodium Salt Polymorph A [Compound (I)]

Fosinopril cesium, viz. [1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline cesium salt dihydrate (III A) [6 gm, 0.008638 moles, obtained from any of the Examples 6–13] was taken in a mixture of dichloromethane (80 ml) and water (40 ml) and cooled to 0–5° C. To this was added an aqueous solution of potassium hydrogen sulfate slowly till the pH is adjusted to 2.5. The organic phase was separated, washed with water (25 ml×2) and the solvent evaporated off. The residue was dissolved in dichloromethane (50 ml) and water was azeotropically removed till the water content in the solvent comes to ca. 0.03%. To this was added a solution of sodium ethyl hexanoate (1.36 gm, 0.008206 moles) in ethyl acetate (65 ml, water content ca. 0.03%) and the mixture stirred for 15 hrs. The solid which crystallises out was filtered, washed with ethyl acetate (40 ml) and dried under vacuum at 40° C. for 6 hrs to give 4.3 gm (86%) of the title compound as a white solid, having purity of 99.5%.

EXAMPLE 17

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Sodium Salt Polymorph A [Compound (I)]

Fosinopril cesium, viz. [1[S*(R*)],2α,4β]-4 cyclohexyl-1-[[[2-methyl-1-(1-oxopropoxy)propoxy)-4-phenylbutyl}acetyl]-(trans)-4-cyclohexyl-L-proline cesium salt dihydrate (III A) [1 gm, 0.00144 moles, obtained from any of the Examples 6–13] was taken in a mixture of dichloromethane (80 ml) and water (40 ml) and cooled to 0–5° C. To this was added an aqueous solution of potassium hydrogen sulfate slowly till the pH is adjusted to 2.5. The organic phase was separated, washed with water (25 ml×2) and the solvent evaporated off. The residue was dissolved in tetrahydrofuran (10 ml) and mixed with a solution of sodium ethyl hexanoate (0.227 gm, 0.00137 moles) in tetrahydrofuran (5 ml) and the mixture stirred for 15 hrs. The solid which crystallises out was filtered and washed with tetrahydrofuran (5 ml) and dried under vacuum at 40° C. for 6 hrs to give 0.7 gm (85%) of the title compound as a white solid, having purity of 99.5%.

EXAMPLE 18

[1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline Sodium Salt Polymorph A [Compound (I)]

Fosinopril cesium, viz. [1[S*(R*)],2α,4β]-4-cyclohexyl-1-[[[2-methyl-1-(1-oxopropoxy)propoxy)-4-phenylbutyl}acetyl]-(trans)-4-cyclohexyl-L-proline cesium salt dihydrate (III A) [1 gm, 0.00144 moles, obtained from any of the Examples 6–13] was taken in a mixture of dichloromethane (80 ml) and water (40 ml) and cooled to 0–5° C. To this was added an aqueous solution of potassium hydrogen sulfate slowly till the pH is adjusted to 2.5. The organic phase was separated, washed with water (25 ml×2) and the solvent evaporated off. The residue was dissolved in toluene (10 ml) and mixed with a solution of sodium ethyl hexanoate (0.227 gm, 0.00137 moles) in ethyl acetate (16 ml) and the mixture stirred for 15 hrs. The solid which crystallises out was filtered and washed with ethyl acetate (5 ml) and dried under vacuum at 40° C. for 6 hrs to give 0.7 gm (85%) of the title compound as a white solid, having purity of 99.5%.

EXAMPLE 19

1[{Hydroxy(4-phenylbutyl)phosphinyl}acetyl]-(trans)-4-cyclohexyl-L-proline [Compound (VIII)]

38 gm (0.0547 moles) of 1 [{2-Methyl-1-(1-oxopropoxy)propoxy)-4-phenylbutyl}acetyl]-(trans)-4-cyclohexyl-L-proline cesium salt as contained in the mother liquor from Example 6 was mixed with water (114 ml) and the mixture cooled to 0–5° C. To this was added an aqueous solution of sodium hydroxide (4.5 gm. 0.112 moles) in 36 ml of water and the mixture stirred for 3 hrs. Ethyl acetate (76 ml) was added to the reaction and the pH adjusted to 2.0–2.1 by addition of Conc. HCl. The organic phase was separated and the solvent evaporated under reduced pressure. The residue was mixed with diisopropyl ether (190 ml) and stirred for 3 hrs. The precipitated solid was filtered, washed with diisopropyl ether and dried at 40° C. to give 20 gm (84%) of the title compound as a white solid.

IR (KJBr): 2925.8, 2852.5, 1716.5, 1625.9, 1604.7, 1450.4, 1136.0 cm$^{-1}$ $^1$H NMR (CDCl$_3$): δ 7.2–6.95 (m, 5H, aromatic protons); 4.5–4.4 (m, 1H, —C$\underline{H}$—COOH); 3.85–3.55 (m+bs, 1H, P—OH and —COOH); 3.05–2.85 (m, 3H, —P—C$\underline{H_2}$—CO— and —N—C$\underline{H}$—); 2.52–2.42 (t, 2H, Ph-C$\underline{H_2}$); 2.28–1.4 (m, 14H); 1.3–0.7 (in, 6H)

EXAMPLE 20

1[{Hydroxy(4-phenylbutyl)phosphinyl}acetyl]-(trans)-4-cyclohexyl-L-proline [Compound (VIII)]

3.9 gm (0.0066 moles) of 1[{2-Methyl-1-oxopropoxy)propoxy)-4-phenylbutyl}acetyl]-(trans)-4-cyclohexyl-L-proline sodium salt as contained in the mother liquor from Example 5 was mixed with water (16 ml) and cooled to 0–5° C. To this was added an aqueous solution of sodium hydroxide (0.546 gm, 0.0136 moles) in 8 ml of water and the mixture stirred for 3 hrs. Ethyl acetate (76 ml) was added to the reaction and the pH adjusted to 2.0–2.1 by addition of Conc. HCl. The organic phase was separated and the solvent evaporated under reduced pressure and the residue was mixed with diisopropyl ether (30 ml) and stirred for 3 hrs. The precipitated solid was filtered, washed with diisopropyl ether and dried at 40° C. to give 1.9 gm of the title compound as a white solid.

EXAMPLE 21

1[{(Hydroxy(4-phenylbutyl)phosphinyl}acetyl]-(trans)-4-cyclohexyl-L-proline benzyl Ester [Compound (VI), Wherein R$^7$ is Hydrogen and R$^8$ is Benzyl Group]

To a solution of 1[{Hydroxy(4-phenylbutyl)phosphinyl}acetyl]-(trans)-4-cyclohexyl-L-proline [(VIII), 50 gm, 0.1149 moles) in cyclohexane (500 ml) was added p-toluene sulfonic acid monohydrate (10 gm) and benzyl alcohol (14.9 gm, 0.1379 moles) and refluxed with simultaneous azeotropic removal of water for 14 hrs. Cyclohexane was distilled out and to the residue ethyl acetate (250 ml) was added and stirred to get a clear solution. The ethyl acetate solution was washed with water (50 ml×2), dried over anhydrous magnesium sulfate and the solvent evaporated to give 59 gm (98%) of the title compound as an oil.

IR(Neat): 2925.8, 2852.5, 1743.5, 1645.2, 1604.7, 1434.9, 1172.6, 960.5 cm$^{-1}$ $^1$H NMR (CDCl$_3$); δ 7.4–7.1 (m, 10H, aromatic protons); 5.25–5.05 (m, 2H, —O—C$\underline{H_2}$-Ph); 4.74.55 (d, 1H, J=9 Hz, —C$\underline{H}$—COOCH$_2$Ph); 4.0–3.8 (m, 1H, —N—C$\underline{H}$—); 3.3–3.15 (m, 1H, —N—C$\underline{H}$—); 3.0–2.5 (m, 4H, —P—C$\underline{H_2}$—CO— and Ph-C$\underline{H_2}$); 2.2–1.5 (m, 14H); 1.3–0.7 (m, 6H)

EXAMPLE 22

1[{Hydroxy(4-phenylbutyl)phosphinyl}acetyl]-(trans)-4-cyclohexyl-L-proline Benzyl Ester [Compound (VI), Wherein R⁷ is Hydrogen and R⁸ is P-Nitro Benzyl Group]

To a solution of 1[{Hydroxy(4-phenylbutyl)phosphinyl}acetyl]-(trans)-4-cyclohexyl-L-proline [(VIII), 0.5 gm, 0.001149 moles) in acetonitrile (5 ml) was added triethylamine (0 25 gm, 002528 moles) and p-nitro benzyl bromide (0.3 gm, 0.001378 moles) added and stirred for 6 hrs. Acetonitrile was evaporated and the residue was dissolved in dichloromethane (10 ml), washed with water and dried over anhydrous magnesium sulfate. The solvent was evaporated and crystallisation of the residue from a mixture of ethylacetate and hexane gave 0.35 gm of the title compound as white solid.

IR (Neat): 2929.7, 2852.5, 1747.4, 1651.0, 1608.5, 1525.6, 1440.7, 1137.9 cm$^{-1}$ $^1$H NMR (CDCl$_3$): δ 8.1–8.0 (d, 2H, J=7.5 Hz, aromatic protons); 7.4–7.3 (d, 2H, J=7.5 Hz, aromatic protons); 7.15–6.95 (m, 5H, aromatic protons); 5.2–5.0 (m, 2H, —O—C$\underline{H}$2-PNB); 4.44.3 (d, 1H, —CH—COO—); 3.85–3.7 (t, 1H); 3.15–3.05 (t, 1H); 2.95–2.75 (m, 2H); 2.55–2.4(t, 2, Ph-C$\underline{H}_2$—); 2.1–1.4 (m, 14H); 1.15–0.7 (m, 6H)

TABLE 1

X-ray (powder) diffraction pattern of the compound of formula (IIIA)

| □ | d | I/I$_1$ | □ | d | I/I$_1$ |
|---|---|---|---|---|---|
| 4.3000 | 20.53270 | 14 | 25.7800 | 3.45302 | 31 |
| 4.6761 | 18.88206 | 65 | 26.3983 | 3.37353 | 13 |
| 4.9800 | 17.73046 | 16 | 26.7986 | 3.32404 | 11 |
| 6.9383 | 12.72990 | 4 | 25.5286 | 3.23753 | 6 |
| 9.0000 | 9.81785 | 18 | 27.9055 | 3.19465 | 14 |
| 9.3400 | 9.46121 | 19 | 28.2600 | 3.15538 | 9 |
| 10.2591 | 8.61556 | 8 | 28.8506 | 3.09211 | 20 |
| 11.1843 | 7.90485 | 17 | 29.3015 | 3.04555 | 5 |
| 13.5200 | 6.54401 | 14 | 30.0261 | 2.97368 | 7 |
| 13.8600 | 6.38423 | 19 | 30.8493 | 2.89618 | 49 |
| 14.3200 | 6.18017 | 9 | 31.1800 | 2.86621 | 5 |
| 14.9000 | 5.94088 | 3 | 31.5400 | 2.83432 | 4 |
| 15.3246 | 5.77722 | 99 | 31.7930 | 2.81234 | 19 |
| 15.9203 | 5.56236 | 39 | 33.2926 | 2.68901 | 44 |
| 16.6550 | 5.31861 | 8 | 34.0710 | 2.62933 | 4 |
| 17.3600 | 5.10417 | 6 | 34.4622 | 2.60037 | 11 |
| 17.8400 | 4.96791 | 23 | 35.3308 | 2.53841 | 17 |
| 18.3005 | 4.84392 | 32 | 36.1300 | 2.48407 | 10 |
| 19.2117 | 4.61618 | 33 | 37.7758 | 2.37954 | 27 |
| 19.8200 | 4.47586 | 7 | 38.3196 | 2.34702 | 5 |
| 20.1837 | 4.39602 | 45 | 38.5848 | 2.33149 | 4 |
| 20.6800 | 4.29163 | 26 | 39.3575 | 2.28748 | 9 |
| 21.0400 | 4.21900 | 17 | 39.8263 | 2.26163 | 10 |
| 21.6800 | 4.09588 | 6 | 40.5967 | 2.22047 | 13 |
| 21.9943 | 4.03805 | 26 | 41.1000 | 2.19443 | 3 |
| 22.5400 | 3.94151 | 26 | 42.3183 | 2.13403 | 8 |
| 22.8624 | 3.88665 | 100 | 43.7725 | 2.06645 | 8 |
| 23.2802 | 3.81784 | 82 | 43.9800 | 2.05718 | 4 |
| 23.8800 | 3.72328 | 4 | 45.1650 | 2.00592 | 3 |
| 24.2400 | 3.66880 | 21 | 45.5060 | 1.99168 | 4 |
| 24.5200 | 3.62753 | 13 | 46.3200 | 1.95856 | 4 |
| 25.0400 | 3.55337 | 27 | 46.5200 | 1.95060 | 4 |
| 25.4000 | 3.50381 | 18 | 47.4679 | 1.91384 | 3 |

The invention claimed is:

1. A process for preparation of fosinopril sodium of formula (I)

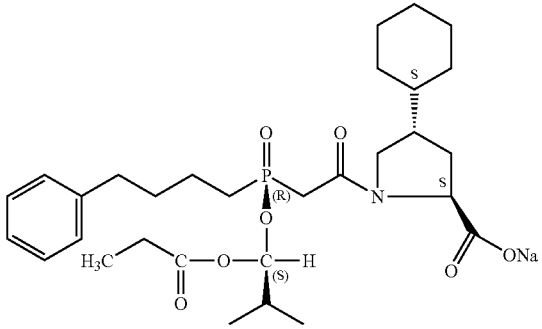

(I)

predominantly in polymorphic Form-A which comprises (a)(i) reacting a compound of formula (IV)

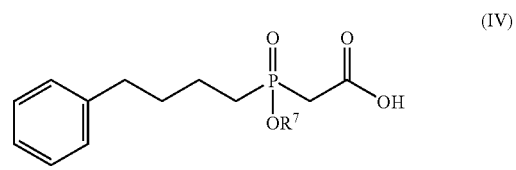

(IV)

wherein R⁷ is lower alkyl of 1–4 carbon atoms with (trans)-4-cyclohexyl-L-proline or salt thereof of formula (V),

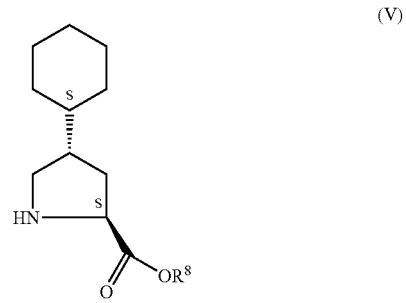

(V)

wherein R⁸ is a group easily removable by hydrogenolysis and is benzyl or benzyl substituted at ortho, meta or para positions by an alkyl, alkoxy, alkanoyl, phenyl, nitro or dialkylamino group in the presence of a solvent and a base to give compound of formula

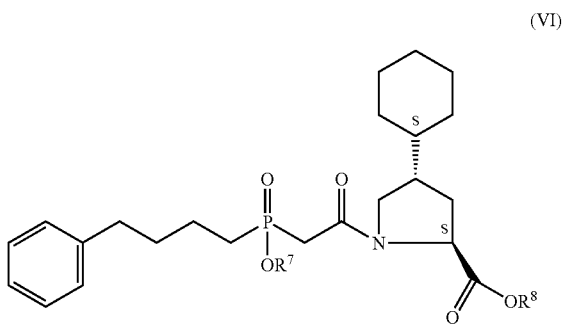

(VI)

wherein R⁷ and R⁸ are as defined above
ii) hydrolysing the alkyl group R⁷ in compound of formula (VI) by reaction with a silyl compound in presence of a alkali metal halide and a solvent to give compound of formula (VI), wherein the group $R^7$ is hydrogen and $R^8$ is as defined above iii) reacting compound of formula (VI) wherein $R^7$ is hydrogen and $R^8$ is as defined above with a compound of formula (VII)

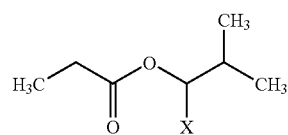

(VII)

wherein X is halogen selected from chlorine, bromine and iodine in the presence of a base and solvent to give compound of formula ($II^a$)

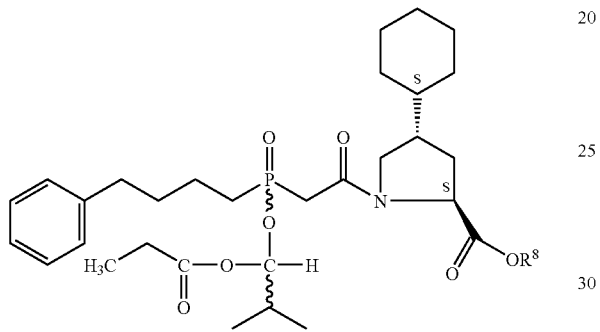

($II^a$)

iv) deprotection of the group $R^8$ in compound of formula ($II^a$) by reacting with hydrogen in presence of palladium on carbon as catalyst in presence of a solvent to give fosinopril as a mixture of four diastereomers (II A), (II B), (II C) and (II D),

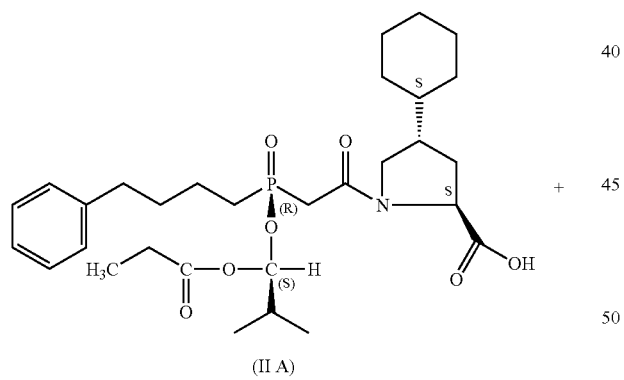

(II A)

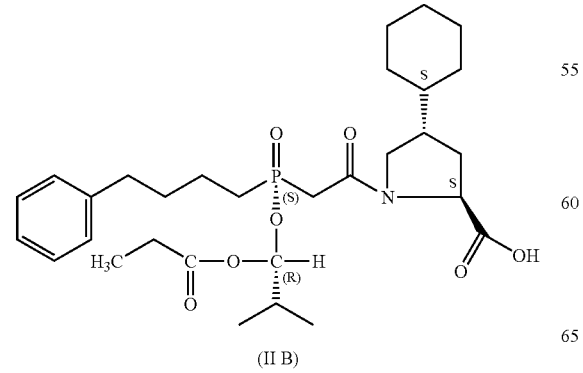

(II B)

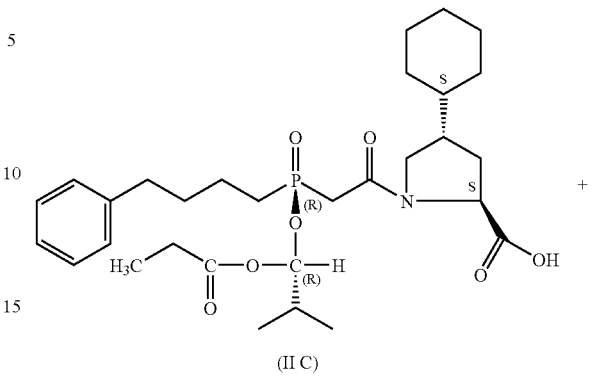

(II C)

(II D)

b) separating fosinopril diastereomer (II A) from the mixture of four diastereomers (II A), (II B), (II C) and (II D) comprising v) mixing together fosinopril mixture of four diastereomers (II A), (II B), (II C) and (II D) with a cesium metal carrier in the presence of a solvent and crystallisation of the mixture of cesium salts thus formed from the same solvent or a mixture of solvents containing 1–10 moles of water with respect to compound (II A)/(II B)/(II C)/(II D) to give compound of formula (III A)

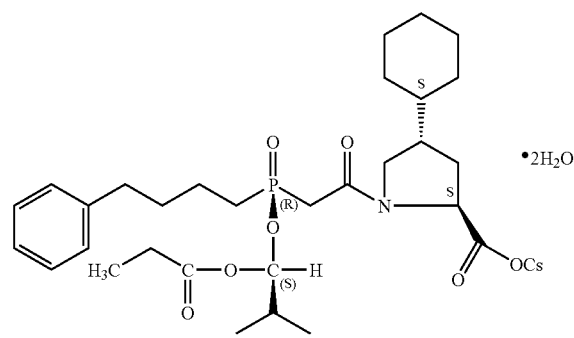

(III A)

vi) reacting compound of formula (III A) with an acid in the presence of a solvent and water to give the fosinopril diastereomer (II A)

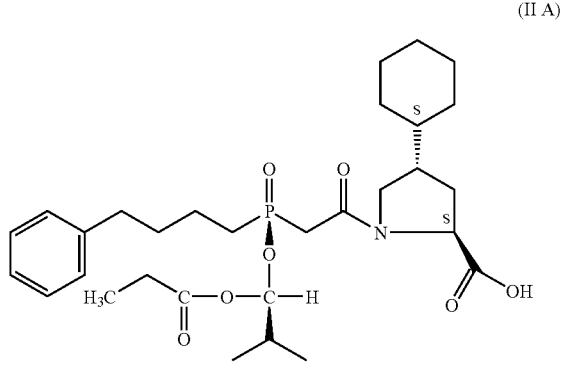

(II A)

and c) converting compound (II A) to fosinopril sodium polymorphic Form-A comprising vii) mixing together compound (II A) with a sodium metal carrier in presence of a solvent or a mixture of solvents to fosinopril sodium of formula (I) and viii) crystallisation of the fosinopril sodium of formula (I) thus formed in the same solvent or mixture of solvents containing water content <0.20% to give fosinopril sodium polymorphic Form-A.

2. A process as claimed in claim 1 wherein said compounds of formulae (IV) and (V) are reacted with each other in the presence of a coupling agent.

3. A process as claimed in claim 2 wherein said coupling agent is dicyclohexylcarbodiimide.

4. A process as claimed in claim 1 wherein said compound of formula (IV) is reacted with said compound of formula (V) after activation its carboxylic function by formation of its mixed anhydride, symmetrical anhydride, acid halide or acid ester.

5. A process as claimed in claim 4 wherein said compound of formula (IV) is reacted with said compound of formula (V) after activation its carboxylic function by formation its mixed anhydride with pivaloyl chloride.

6. The process of claim 1 wherein said solvent employed in step (a)(i) is selected from the group consisting of one or more of acetonitrile, dichloromethane, dichloroethane, dioxane, N,N-dimethyl acetamide, N,N-dimethyl formamide and tertrahydrofuran, with acetonitrile, dichloromethane and tetrahydrofuran preferred.

7. The process of claim 1 wherein said base employed in step (a)(i) is selected from the group consisting of one or more of triethylamine, tripropylamine, diazabicycloundecene and N-methylmorpholine.

8. The process of claim 7, wherein the base is employed in a mole ratio to compound of formula (IV) of within the range from about 1:3, preferably from about 1:1.5 to 1:2.

9. The process of claim 1, wherein the solvent employed in step (a)(ii) is selected from the group consisting of one or more of acetonitrile, dichloromethane, dichloroethane, dioxane, N,N-dimethyl acetamide, N,N-dimethyl formamide, tetrahydrofuran, toluene and xylene.

10. The process of claim 1 wherein said silyl compound employed in step (a)(ii) is selected from trimethylchlorosilane, trimethylbromsilane and hexadimethylsilazane.

11. The process of claim 1, wherein the alkali metal halide employed in step (a)(ii) is selected from sodium bromide, sodium iodide, potassium bromide and potassium iodide.

12. The process of claim 1, wherein the solvent employed in step (a)(iii) is selected from the group consisting of one or more acetonitrile, dichloromethane, dichloroethane, ethyl acetate, N,N-dimethyl acetamide, N,N-dimethyl formamide, tetrahydrofuran, toluene and xylene, with ethyl acetate, toluene and xylene preferred.

13. The process of claim 1 wherein said compound (VI), wherein $R^7$ is hydrogen is employed in a molar ratio to compound (VII) of within the range of about 1:4, preferably from about 1:1.5 to about 1:2.

14. The process of claim 1 (a)(iii), wherein the base employed in step (a)(iii) is selected from triethylamine, pyridine, tripropylamine, diazabicycloundecene and N-methylmorpholine.

15. The process of claim 14, wherein the base is employed in a molar ratio to compound (VI), wherein $R^7$ is hydrogen of within the range of about 1:4, preferably from about 1:1.5 to about 1:2.

16. The process of claim 1 wherein the solvent employed in step (a)(iv) is selected from the group consisting of one or more acetonitrile, ethanol, ethyl acetate, methanol, N,N-dimethyl acetamide, N,N-dimethyl formamide, tetrahydrofuran, toluene and xylene, with dichloromethane, ethyl acetate, toluene and xylene preferred.

17. The process of claim 1 wherein said cesium metal carrier is selected from cesium carbonate, cesium bicarbonate and cesium ethyl hexanoate.

18. The process of claim 17, wherein the cesium metal carrier is employed in a molar ratio to compound (II A)/(II B)/(II C)/(II D) of within the range of about 1:3, preferably from about 1:1.5.

19. The process of claim 1, wherein the solvent employed in step (b)(v) is selected from one or more of acetone, acetonitrile, dichloromethane, dichloroethane, diethyl ether, diisopropyl ether, dioxane, ethyl acetate, methyl ethyl ketone, methyl isobutyl ketone, N,N-dimethyl acetamide, N,N-dimethyl formamide, tertiary butyl methyl ether, tetrahydrofuran, toluene and xylene or mixtures thereof.

20. The process of claim 1 wherein in step (b)(v), the water content in the solvent during crystallisation of compound (III A) is in a molar ratio of 1:10 to compound (II A)/(II B)/(II C)/(II D), preferably of within the range of about 1:5.

21. The process of claim 1 wherein the acid employed in step (b)(vi) is selected from hydrochloric acid, nitric acid, sulphuric acid and potassium hydrogen sulfate, with potassium hydrogen sulfate preferred.

22. The process of claim 1 wherein the solvent employed in step (b)(vi) is selected from dichloromethane, dichloroethane, diethyl ether, diisopropyl ether, ethyl acetate, methyl ethyl ketone, methyl isobutyl ketone, N,N-dimethyl acetamide, N,N-dimethyl formamide, tetrahydrofuran, toluene and xylene.

23. The process of claim 1, wherein in said step (c)(vii), the sodium metal carrier is selected from sodium acetate, sodium carbonate, sodium bicarbonate and sodium ethyl hexanoate.

24. The process of claim 1, wherein in said step (c)(vii), the solvent is selected from one or more of acetonitrile, dichloromethane, dichloroethane, diethyl ether, diisopropyl ether, dioxane, ethyl acetate, methyl ethyl ketone, methyl isobutyl ketone, N,N-dimethyl acetamide, N,N-dimethyl formamide, tetrahydrofuran, toluene and xylene, with dichloromethane and ethyl acetate preferred.

25. The process of claim 1, wherein in said step (c)(viii), the water content of the total solvents is within the range from about 0.03 to 0.05%.

26. The process of claim 1 wherein said solvent in step (a) is selected from one or more of acetone, acetonitrile, dichloromethane, ethyl acetate and mixtures thereof or a mixture of any one or more thereof with diethyl ether and diisopropyl ether.

27. The process of claim 26 wherein said alkali metal is sodium or pottasium.

28. The process of claim 26 wherein prior to mixing with cesium salt in step (d), said free acid is treated with an amine compound and again reacted with an acid to obtain a free acid.

29. The process as claimed in claim 26 wherein said mixing with said cesium salt is carried out at anhydrous or near anhydrous conditions.

30. The process of claim 26 wherein acid is an organic or inorganic acid.

* * * * *